United States Patent [19]

Shibahara et al.

[11] Patent Number: 4,645,769
[45] Date of Patent: Feb. 24, 1987

[54] 1-OXA-1-DETHIA-CEPHALOSPORIN COMPOUNDS AND ANTIBACTERIAL AGENT COMPRISING THE SAME

[75] Inventors: Seiji Shibahara, Machida; Tsuneo Okonogy, Yokohama; Yasushi Murai, Yokosuka; Shunzo Fukatsu, Tokyo; Taro Niida, Yokohama, all of Japan; Burton G. Christensen, Cliffside, N.J.; Tadashi Wakazawa, Yokohama, Japan

[73] Assignee: Merck & Co., Inc., Rahway, N.J.

[21] Appl. No.: 705,799

[22] Filed: Mar. 1, 1985

[51] Int. Cl.$^4$ .................. A01N 43/90; C07D 498/04
[52] U.S. Cl. ........................................ 514/210; 544/90
[58] Field of Search ........................... 544/90; 514/210

[56] References Cited

U.S. PATENT DOCUMENTS

| | | | |
|---|---|---|---|
| 4,226,864 | 10/1980 | Narisada et al. | 544/90 X |
| 4,226,866 | 10/1980 | Christensen et al. | 544/90 X |
| 4,307,116 | 12/1981 | Large et al. | 514/203 X |
| 4,366,316 | 12/1982 | Yoshioka et al. | 544/90 |
| 4,438,114 | 3/1984 | Boberg et al. | 544/90 X |
| 4,504,477 | 3/1985 | O'Callaghan et al. | 514/203 |
| 4,534,898 | 8/1985 | Shibahara et al. | 544/90 X |

FOREIGN PATENT DOCUMENTS

| | | |
|---|---|---|
| 75805 | 4/1983 | European Pat. Off. . |
| 76463 | 4/1983 | European Pat. Off. . |
| 88853 | 9/1983 | European Pat. Off. . |
| 99580 | 2/1984 | European Pat. Off. . |
| 89289 | 7/1980 | Japan . |
| 154980 | 12/1980 | Japan . |
| 90590 | 5/1983 | Japan . |

OTHER PUBLICATIONS

Morin et al., Chemistry and Biology of β-Lactam Antibiotics, vol. 2 (1982) Academic Press, New York, pp. 1–98.

*Primary Examiner*—Richard L. Raymond
*Attorney, Agent, or Firm*—Raymond M. Speer; Hesna J. Pfeiffer

[57] ABSTRACT

The subject invention includes a 1-oxa-1-dethia-cephalosporin compound represented by the general formula (1)

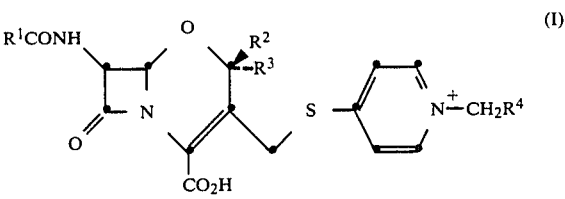

wherein $R^1$ is a group of the formula:

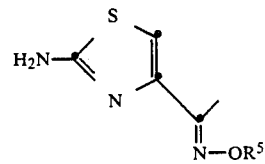

where $R^5$ is a methyl group, an ethyl group, a carboxymethyl group or a 2-carboxy isopropyl group, or $R^1$ is a group of the formula:

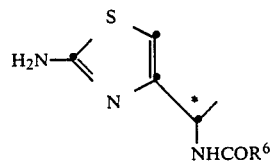

where $R^6$ is a hydrogen atom, a 4-ethyl-2,3-dioxopiperazine-1-yl group, a 3,4-dihydroxy phenyl group or a 5- and 6-membered heterocyclic radical having 2 ring nitrogens as the sole hetero substituent in the ring and having at least one hetero group on the carbon adjacent to the ring nitrogens.

4 Claims, No Drawings

1-OXA-1-DETHIA-CEPHALOSPORIN COMPOUNDS AND ANTIBACTERIAL AGENT COMPRISING THE SAME

DETAILED DESCRIPTION OF THE INVENTION

This invention relates to a novel antibacterial 1-oxa-1-dethiacephalosaporin compound.

We, the present inventors, have made extensive researches in an attempt to seek for and to synthesize such a new cephalosporin compound which exhibits a wide range of antibacterial spectrum and which is active against a variety of resistant bacteria. As a result, the present inventors have now succeeded in preparing 1-Oxa-1-dethia cephalosporin compounds which are effective as an antibacterial agent in therapeutic treatment of animals including man.

Thus the present inventors have succeeded in the synthesis of a 1-oxa-1-dethiacephalosporin compound of the general formula (1):

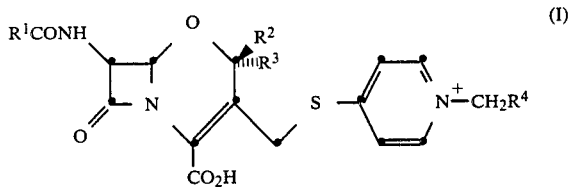

wherein $R^1$ is a group of the formula:

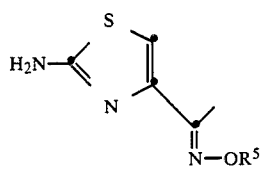

where $R^5$ is a methyl group, an ethyl group, a carboxymethyl group, or a 2-carboxyisopropyl group, or $R^1$ is a group of the formula:

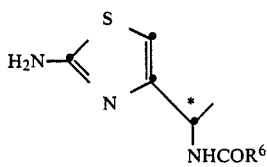

where $R^6$ is a hydrogen atom, a 4-ethyl-2,3-dioxopiperazine-1-yl group, a 3,4-dihydroxy phenyl group or a 5- and 6-membered heterocyclic radical having 2 ring nitrogens as the sole hetero substituent in the ring and having at least one hetero group on the carbon adjacent to the ring nitrogens of the formula:

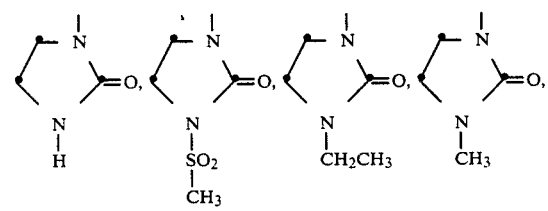

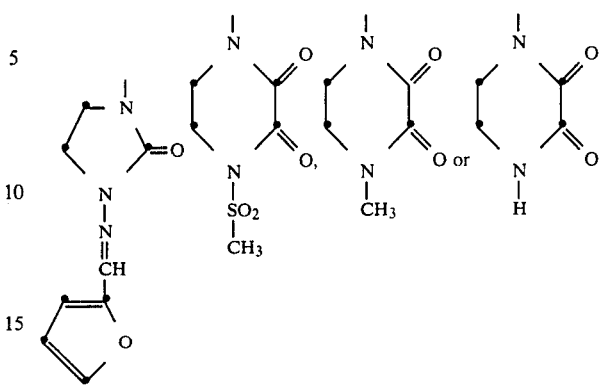

and the carbon atom to which the asterisk * is attached shows (R)-configuration or (S)-configuration or a mixture of these configurations; both of $R^2$ and $R^3$ are each a hydrogen atom either one of $R^2$ and $R^3$ is a hydrogen atom and the other a methyl group; $R^4$ is a hydrogen atom, a methyl group, a carboxyl group, a trifluoromethyl group or a monofluoromethyl group and $R^7$ is a carboxyl protecting group. And we have found that the 1-oxa-1-dethia cephalosporin compounds bearing 1-alkylpyridine-4-thio-yl methyl group at the 3-position thereof show a wide range of antibacterial activity against gram-positive and gram-negative bacteria including a variety of resistant bacteria, especially β-lactamase producing Pseudomonas species, and that these compounds exhibit an excellent activity as an antibacterial agent when administered intramuscularly or intravenously to the animals.

Japanese patent application first publication "KOKAI" Nos. 90590/83 and 89289/80 disclose such cephalosporin compounds which have at the 3-position thereof a 1-alkylpyridine-4-thio-yl-methyl group, but these first publication have no description in respect of the 1-oxa-1-dethiacephalosporin compounds. The compounds of the formula (I) mentioned above are thus novel compounds.

It is generally known that, such 1-oxa-1-dethiacephalosporin compounds having a 2-amino-thiazole-4-acetic acid derivatives as a substituent on the 7-amino group thereof are inferior in the antibacterial activity to the corresponding cephalosporins (R. B. Molin, M. Gorman "Chemistry and Biology of β-lactam Antibiotics", Vol. 2, pages 1–98 (1982), Academic Press, New York). While, the present inventors have found that though the compound of the general formula (I) according to this invention has a 2-aminothiazole-4-acetic acid derivatives as a substituent on the 7-amino group, the new compound of this invention exhibits an excellent antibacterial activity against Streptococcus faecalis against which the corresponding cephalosporins (as referred to in said Japanese patent application first publication "KOKAI" No. 154980/80) are ineffective, and that the antibacterial activity of the 1-oxa-1-dethiacephalosporin compounds of the formula (I) can be further enhanced by introducing a methyl group into the 2-position thereof and appropriately selecting the substituents: $R^4$, $R^5$ or $R^6$, in the compounds of the formula (I). In this way, this invention have been accomplished.

According to a first aspect of this invention therefore, there is provided a 1-oxa-1-dethiacephalosporin compound of the general formula (1) mentioned above and a pharmaceutically acceptable hydrate, salt or ester thereof.

Typical examples of the compounds of the general formula (1) include the following:

Structures of the compounds (1)

| Compound No. | $R^1$ | $R^2$ | $R^3$ | $R^4$ |
|---|---|---|---|---|
| 1 | $C(Me)_2CO_2H$ | $CH_3$ | H | $CH_3$ |
| 2 | $C(Me)_2CO_2H$ | $CH_3$ | H | $CH_2CH_3$ |
| 3 | $C(Me)_2CO_2H$ | $CH_3$ | H | $CH_2CH_2F$ |
| 4 | $C(Me)_2CO_2H$ | $CH_3$ | H | $CH_2CF_3$ |
| 5 | $C(Me)_2CO_2H$ | $CH_3$ | H | $CH_2CO_2H$ |
| 6 | $CH_3$ | $CH_3$ | H | $CH_2CF_3$ |
| 7 | $CH_3$ | $CH_3$ | H | $CH_2CO_2H$ |
| 8 | $CH_2CH_3$ | $CH_3$ | H | $CH_2CO_2H$ |
| 9 | $CH_2CO_2H$ | $CH_3$ | H | $CH_2CO_2H$ |
| 10 | $CH_3$ | H | H | $CH_3$ |
| 11 | $CH_3$ | H | H | $CH_2CO_2H$ |
| 12 | $CH_2CH_3$ | H | H | $CH_2CO_2H$ |
| 13 | $CH_2CO_2H$ | H | H | $CH_3$ |
| 14 | $C(Me)_2CO_2H$ | H | H | $CH_3$ |
| 15 | $C(Me)_2CO_2H$ | H | H | $CH_2CH_2F$ |
| 16 | $C(Me)_2CO_2H$ | H | H | $CH_2CF_3$ |
| 17 | $C(Me)_2CO_2H$ | $CH_3$ | H | $CH(CH_2F)_2$ |
| 18 | $CH_2CO_2H$ | $CH_3$ | H | $CH_2CH_3$ |
| 19 | $CH_2CO_2H$ | $CH_3$ | H | $CH_2CH_2F$ |

Structures of the compounds (2)

| Compound No. | $R^6$ | $R^2$ | $R^3$ | $R^4$ |
|---|---|---|---|---|
| 20 | (piperazine-2,3-dione-yl) | H | H | $CH_3$ |
| 21 | (piperazine-2,3-dione-yl) | H | H | $CH_2CO_2H$ |

Chemical Names of the Compounds

No. 1: (6R,7R)-7-((Z)-2-(2-Aminothiazole-4-yl)-2-(2-carboxyprop-2-oxyimino)acetamide)-(2S)-2-methyl-3-(1-methyl-pyridinium-4-ylthiomethyl)-1-oxa-1-oxa-1-dethiaceph-3-em-4-carboxylate (Sodium Salt)

No. 2: (6R,7R)-7-((Z)-2-(2-Aminothiazole-4-yl)-2-(2-carboxyprop-2-oxyimino)acetamide)-(2S)-2-methyl-3-(1-ethyl-pyridinium-4-ylthiomethyl)-1-oxa-1-dethiaceph-3-em-4-carboxylate (Sodium Salt)

No. 3: (6R,7R)-7-((Z)-2-(2-Aminothiazole-4-yl)-2-(2-carboxyprop-2-oxyimino)acetamide)-(2S)-2-methyl-3-(1-(2-fluoroethyl)pyridinium-4-ylthiomethyl)-1-oxa-1-dethiaceph-3-em-4-carboxylate (Sodium Salt)

No. 4: (6R,7R)-7-((Z)-2-(2-Aminothiazole-4-yl)-2-(2-carboxyprop-2-oxyimino)acetamide)-(2S)-2-methyl-3-(1-(2,2,2-trifluoroethyl)pyridinium-4-ylthionethyl)-1-oxa-1-dethia-3-ceph-4-carboxylate (Sodium Salt)

No. 5: (6R,7R)-7-((Z)-2-(2-Aminothiazole-4-yl)-2-(2-carboxyprop-2-oxyimino)acetamide)-(2S)-2-methyl-3-(1-carboxymethylpyridinium-4-ylthiomethyl-1-oxa-1-dethiaceph-3-em-4-carboxylate (Sodium Salt)

No. 6: (6R,7R)-7-((Z)-2-(2-Aminothiazole-4-yl)-2-methoxyiminoacetamide)-(2S)-2-methyl-3-(1-(2,2,2-trifluoroethyl)pyridinium-4-ylthiomethyl)-1-oxa-1-dethiaceph-3-em-4-carboxylate No. 7: (6R,7R)-7-((Z)-2-(2-Aminothiazole-4-yl)-2-methoxyiminoacetamide)-(2S)-2-methyl-3-(1-carboxymethylpyridinium-4-ylthiomethyl)-1-oxa-1-dethiaceph-3-em-4-carboxylate (Sodium Salt)

No. 8: (6R,7R)-7(Z)-2-(2-Aminothiazole-4-yl)-2-ethoxyiminoacetamide)-(2S)-2-methyl-3-(1-carboxymethylpyridinium-4-ylthiomethyl)-1-oxa-1-dethiaceph-3-em-4-carboxylate (Sodium Salt)

No. 9: (6R,7R)-7-((Z)-2-(2-Aminothiazole-4-yl)-2-carboxymethoxyiminoacetamide)-(2S)-2-methyl-3-(1-carboxymethylpyridinium-4-ylthiomethyl)-1-oxa-1-dethiaceph-3-em-4-carboxylate (Sodium Salt)

No. 10: (6R,7R)-7-((Z)-2-(2-Aminothiazole-4-yl)-2-methoxyiminoacetamide)-3-(1-methylpyridinium-4-yl-thiomethyl)-1-oxa-1-dethiaceph-3-em-4-carboxylate No. 11: (6R,7R)-7-((Z)-2-(2-Aminothiazole-4-yl)-2-methoxyiminoacetamide)-3-(1-carboxymethyl-pyridinium-4-yl-thiomethyl)-1-oxa-1-dethiaceph-3-em-4-carboxylate (Sodium Salt)

No. 12: (6R,7R)-7-((Z)-2-(2-Aminothiazole-4-yl)-2-ethoxyiminoacetamido)-3-(1-carboxymethylpyridinium-4-ylthiomethyl)-1-oxa-1-dethiaceph-3-em-4-carboxylate (Sodium Salt)

No. 13: (6R,7R)-7-((Z)-2-(2-Aminothiazole-4-yl)-2-carboxymethoxyiminoacetamide)-3-(1-methylpyridinium-4-ylthiomethyl)-1-oxa-1-dethiaceph-3-em-4-carboxylate (Sodium Salt)

No. 14: (6R,7R)-7-((Z)-2-(2-Aminothiazole-4-yl)-2-(2-carboxyprop-2-oxyimino)acetamide-3-(1-methyl-pyridinium-4-yl-thiomethyl)-1-oxa-1-dethiaceph-3-em-4-carboxylate (Sodium Salt)

No. 15: (6R,7R)-7-((Z)-2-(2-Aminothiazole-4-yl)-2-2-carboxyprop-2-oxyimino)acetamide)-3-((2-fluoroethyl)pyridinium-4-ylthiomethyl)-1-oxa-1-dethiaceph-3-em-4-carboxylate No. 16: (6R,7R)-7-((Z)-2-(2-Aminothiazole-4-yl)-2-(2-carboxyprop-2-oxyimino)acetamide)-3-(1-(2,2,2-trifluoroethyl)-pyridinium-4-ylthiomethyl)-1-oxa-1-dethiaceph-3-em-4-carboxylate (Sodium Salt)

No. 17: (6R,7R)-7-((Z)-2-(2-Aminothiazole-4-yl)-2-(2-carboxyprop-2-oxyimino)acetamide)-(2S)-2-methyl-3-(1-(1,3-difluoroprop-2-yl)-pyridinium-4-ylthiomethyl)-1-oxa-1-dethiaceph-3-em-4-carboxylate (Sodium Salt)

No. 18: (6R,7R)-7-((Z)-2-(2-Aminothiazole-4-yl)-2-carboxymethoxyiminoacetamide)-(2S)-2-methyl-3-(1-methylpyridinium-4-ylthiomethyl)-1-oxa-1-dethiaceph-3-em-4-carboxylate (Sodium Salt)

No. 19: (6R,7R)-7-((Z)-2-(2-Aminothiazole-4-yl)-2-carboxymethoxyiminoacetamide)-(2S)-2-methyl-3-(1-(2-fluoroethyl)pyridinium-4-ylthiomethyl)-1-oxa-1-dethiaceph-3-em-4-carboxylate (Sodium Salt)

No. 20: (6R,7R)-7-(DL-2-(2-Aminothiazole-4-yl)-2-(4-ethyl-2,3-dioxopiperazine-1-ylcarboxamide)acetamide)-3-(1-methylpyridinium-4-ylthiomethyl)-1-oxa-1-dethiaceph-3-em-4-carboxylate (Sodium Salt)

No. 21: (6R,7R)-7-(DL-2-(2-Aminothiazole-4-yl)-2-(4-ethyl-2,3-dioxopiperazine-1-ylcarboxamide)acetamide)-3-(1-carboxymethylpyridinium-4-yl-thiomethyl)-1-oxa-1-dethiaceph-3-em-4-carboxylate (Sodium Salt)

The above mentioned compound numbers are referred to in Tables and Examples given hereinafter.

The compound of the general formula (I) according to this invention includes a solvate, particularly hydrate of said compound (I). Moreover, this invention also covers a non-toxic salt and a non-toxic ester of the compounds of the formula (I), and in particular, a metabolically unstable ester thereof, as will be described later. By the term "non-toxic" is meant "pharmaceutically acceptable".

The above-exemplified representatives of the novel compounds of the formula (I) according to this invention have the following advantages:

(a) As will be clear from Table I given below which shows antibacterial spectra of the test compounds No. 1 to No. 18 against a variety of gram-positive and gram-negative bacteria as determined in vitro in term of the minimum inhibitory concentration (MIC) of said test compounds against said bacteria, the compounds of this invention exhibit a high antibacterial activity against a wide range of bacteria. For comparison, MIC of Latamoxef and Ceftazidime are also indicated in the Table 1.

Also be apparent from the Table 1, not only the compounds of this invention exhibit a practically effective, high antibacterial activity against a variety of bacteria, including the resistance strains thereof, but also those compounds as indicated in Examples 6, 7, 8, 10, 11 and 12 in particular, show such a remarked advantage that they are effective against Streptococcus faecalis. Besides, the compounds of Examples 1, 2, 3, 4, 6, 9, 14, 15 and 16 advantageously are also effective against Pseudomonas aeruginosa which is clinically very important.

(b) The novel compounds of this invention have a practically enough blood serum concentration as shown on Table 2 below:

TABLE 1

Minimum Inhibitory Concentration (MIC) (mcg/ml)

| Test Organisms | Compound No. 1 | Compound No. 2 | Compound No. 3 | Compound No. 4 | Compound No. 5 | Compound No. 6 | Compound No. 7 | Compound No. 8 | Compound No. 9 | Compound No. 10 |
|---|---|---|---|---|---|---|---|---|---|---|
| Staphylococcus aureus 209 P JC-1 | 1.56 | 0.78 | 0.78 | 1.56 | 12.5 | 0.20 | 0.39 | 0.39 | 6.25 | 0.10 |
| StrEptococcus faecalis ATCC 8043 | 50 | 50 | 25 | 50 | 50 | 12.5 | 12.5 | 6.25 | 50 | 1.56 |
| Esherichia coli NIHJ JC-2 | 0.20 | 0.20 | 0.20 | 0.20 | 0.39 | 0.05 | <0.025 | 0.10 | 0.10 | <0.025 |
| Esherichia coli TEM DC-2 | 0.5 | — | — | — | — | — | — | — | — | — |
| Enterobacter cloacae P99 | 1.0 | — | — | — | — | — | — | — | — | — |
| Klebsiella pneumoniae PCI 602 | 0.20 | 0.20 | 0.20 | 0.39 | 0.39 | 0.10 | 0.025 | 0.05 | 0.10 | 0.025 |
| Salmonella typhimurium LT-2 | 0.05 | <0.025 | <0.025 | 0.05 | 0.10 | <0.025 | <0.025 | 0.05 | <0.025 | <0.025 |
| Proteus morganii 1510 | 0.39 | 0.10 | 0.20 | 0.20 | 1.56 | 6.25 | 0.78 | 0.78 | 0.78 | 1.56 |
| Citrobacter freundii GN-346 | 0.78 | 0.78 | 0.78 | 1.56 | 3.13 | 50 | 6.25 | 6.25 | 12.5 | 1.56 |
| Pseudomonas aeruginosa MB-3833 | 3.13 | 3.13 | 1.56 | 3.13 | 3.13 | 3.13 | 12.5 | 12.5 | 3.13 | 6.25 |
| Pseudomonas aeruginosa E-2 | 3.13 | 3.13 | 1.56 | 3.13 | 6.25 | 3.13 | 12.5 | 12.5 | 3.13 | 25 |
| Pseudomonas aeruginosa RPL-11 | 4.0 | — | — | — | — | — | — | — | — | — |

| Test Organisms | Compound No. 11 | Compound No. 12 | Compound No. 13 | Compound No. 14 | Compound No. 15 | Compound No. 16 | Compound No. 17 | Compound No. 18 | Compound No. 19 | Compound No. 20 |
|---|---|---|---|---|---|---|---|---|---|---|
| Staphylococcus aureus 209 P JC-1 | 0.39 | 0.39 | 1.56 | 1.56 | 6.25 | 3.13 | 0.78 | 0.78 | 3.13 | 0.39 |
| Streptococcus faecalis ATCC 8043 | 0.78 | 6.25 | 50 | >100 | 50 | >100 | 25 | 25 | >100 | >100 |
| Esherichia coli NIHJ JC-2 | <0.025 | <0.025 | <0.025 | 0.10 | 0.10 | 0.10 | 0.025 | 0.05 | 0.78 | 0.10 |
| Esherichia coli TEM DC-2 | — | — | 1.0 | 0.25 | — | 0.03 | — | — | — | — |
| Enterobacter cloacae P99 | — | — | 64.0 | 128 | — | 128 | — | — | — | — |
| Klebsiella pneumoniae PCI 602 | 0.025 | 0.025 | 25 | 0.10 | 0.10 | 0.10 | 0.05 | 0.10 | 0.39 | 0.20 |
| Salmonella typhimurium LT-2 | <0.025 | <0.025 | <0.025 | <0.025 | 0.5 | <0.025 | <0.025 | <0.025 | 0.10 | 0.20 |
| Proteus morganii 1510 | 6.20 | 12.5 | 1.56 | 3.13 | 6.25 | 6.25 | 0.20 | 0.10 | 0.20 | 6.25 |
| Citrobacter freundii GN-346 | 12.5 | 12.5 | 6.25 | 50 | 50 | 25 | 1.56 | 1.56 | 1.56 | 25 |

TABLE 1-continued

| | Minimum Inhibitory Concentration (MIC) (mcg/ml) | | | | | | | | |
|---|---|---|---|---|---|---|---|---|---|
| Pseudomonas aeruginosa MB 3833 | 25 | 12.5 | 6.25 | 1.56 | 3.13 | 1.56 | 1.56 | 1.56 | 3.13 | 100 |
| Pseudomonas aeruginosa E-2 | 50 | 25 | 6.25 | 1.56 | 3.13 | 1.56 | 1.56 | 1.56 | 3.13 | 25 |
| Pseudomonas aeruginosa RPL 11 | — | — | 128 | 64 | — | 32.0 | — | — | — | — |

TABLE 1-(3)

| Test Organisms | Compound No. 21 | Latamoxef | Ceftazidime |
|---|---|---|---|
| Staphylococcus aureus 209 P JC-1 | 1.56 | 3.13 | 1.56 |
| Streptococcus faecalis ATCC 8043 | 50 | 25 | 50 |
| Esherichia coli NIHJ JC-2 | 0.05 | 0.10 | 0.10 |
| Esherichia coli TEM DC-2 | — | — | 0.5 |
| Enterobacter cloacae P99 | — | — | 64.0 |
| Klebsiella pneumoniae PCI 602 | 0.05 | 0.20 | 0.10 |
| Salmonella typhimurium LT-2 | 0.10 | 0.05 | 0.05 |
| Proteus morganii 1510 | 12.5 | 0.20 | 12.5 |
| Citrobacter freundii GN-346 | >100 | 1.56 | 25 |
| Pseudomonas aeruginosa MB-3833 | >100 | 6.25 | 0.78 |
| Pseudomonas aeruginosa E-2 | >100 | 6.25 | 0.78 |
| Pseudomonas aeruginosa RPL-11 | — | — | 3.0 |

TABLE 2

| | Concentration in Blood Serum (mcg/ml) | | | |
|---|---|---|---|---|
| Compound Tested | 1/12 | ¼ | ½ | 1 hour |
| NO. 1 | 14.5 | 18.5 | 10.6 | 2.2 |
| NO. 9 | 36 | 32 | 25 | 5.1 |
| NO. 14 | 18 | 11.5 | 8.8 | 5.0 |
| NO. 16 | 16 | 20 | 11 | 2.4 |
| Ceftazidime | 13 | 20 | 11.5 | 6.3 |

In order to demonstrate the blood serum concentration the test samples was given at a dosage of 25 mg/Kg subcutaneously to mice (three mice in each group, average weight 20 g), and blood was collected at a specified time. The concentration of the compound in the serum was determined by bioassay using Escherichia coli as assay microorganism.

(c) Additionally a practical in vivo efficacy of the novel compounds of this invention as an antibiotic for animals is demonstrated shown on Table 3.

TABLE 3

| Efficacy in Mice Infected with Staphylococus aureus (Smith I) or Pseudomonas aeruginosa (GN 10362) | | |
|---|---|---|
| | (ED 50, mg/kg) | |
| | St. aureus | Ps. aeruginosa |
| Compound 1 | 0.028 | 0.16 |
| Compound 14 | 0.016 | 0.13 |
| Latamoxef | 0.67 | 2.9 |
| Ceftazidime | — | 0.22 |

A systemic infection was produced by intraperitoneal injection of the appropriate pathogen to mice (five male mice in each group, average body weight 20 g), and the mice were received single subcutaneous dose of the compound one hour after the infection. The mice were observed for death for seven days at which time the median effective dose (Ed-50) was calculated.

As demonstrated by the foregoing tests: (a), (b) and (c), the novel compound of the formula (1) according to this invention has remarkably excellent properties as the antibacterial agent, so that it is a useful antibiotic which can be administered parenterally or orally for curative or preventative treatment of bacterial infections in mammalian animals, including man.

According to a second aspect of this invention, therefore, there is provided an antibacterial agent which comprises at least one of a 1-oxa-1-dethiacephalosporin compound represented by the aforesaid general formula (I), and a non-toxic hydrate, a non-toxic salt or a non-toxic ester of said compound as the active ingredient.

Non-toxic salt, that is, the pharmaceutically acceptable salt of the compound of general formula (I) includes conventional non-toxic salts, carboxylate, which may be formed by reaction of the carboxyl group present in said compound with a base, expecially such salts with an inorganic base, for example, alkaline metal salts such as sodium or potassium salt and alkaline earth metal salts such as calcium, magnesium or zinc salt; such addition salts with a basic amino acid, for example, lysine, arginine, ornithine or histidine; and such addition salts with an organic amine salt or other basic salts which will normally form a salt with cephalosporin.

Other non-toxic salt of the compound (1) according to this invention include those which may be formed by addition to the amino group or other basic group of an inorganic acid such as hydrochloric, hydrobromic, sulfuric, nitric or phosphoric acid, of an organic carboxylic acid or organic sulfuric acid such as trifluoroacetic, benzenesulfonic, methansulfonic, maleic, tartaric or p-toluenesulfonic acid, and of an acidic amino acid such as aspartic or glutamic acid, and further they may include intermolecular or intramolecular salts.

The non-toxic ester of the compound (1) according to this invention include those of the carboxyl group present in said compound with a pharmaceutically acceptable ester-forming group. Among them are preferred such methabolically unstable esters, which carry an ester-forming group cleavable upon hydrolysis in vivo. Examples of such ester-forming group include acetoxymethyl, pivaloyloxymethyl, ethoxycarbonyloxyethyl, phthalidyl and phenyl groups and the like.

For use as antibacterial agent, the compound (1) of this invention may be given orally or parenterally to adult at a unit dosage of 50 to 1,500 mg and preferably of 100 to 1,000 mg once to five times per day when it is administered for therapeutic treatment of bacterial infection in man. The antibacterial agent according to this invention may usually be composed of the compound of this invention in association with a solid or liquid excipient, and it may be formulated into solid preparations such as tablets, capsules, powder and pre-treated powder, or into liquid preparations such as injectable solutions, intravenous drip solution, suspension and syrup.

Solid or liquid excipient used for this purpose may be any one known in this field of the art. As stated above, the preparations so formed may preferably contain the compound of this invention at an amount required for the unit dosage of the compound for adult indicated above.

The compound (1) according to this invention may be produced, for example, by reacting a 1-oxa-1-dethiacephem compound of the general formula (III):

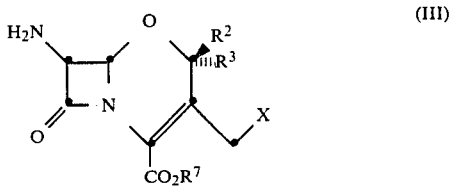

wherein both of $R^2$ and $R^3$ are each a hydrogen atom, or either one of $R^2$ and $R^3$ are each a hydrogen atom and the other a methyl group, $R^7$ is a carboxyl-protecting group, and X is a chlorine, bromine or iodine atom, with a carboxylic acid of the general formual (IV):

wherein $R^1$ is as defined in the general formula (I) hereinbefore, or with a functional derivative thereof, to give a 7-N-acylation product of the general formula (V):

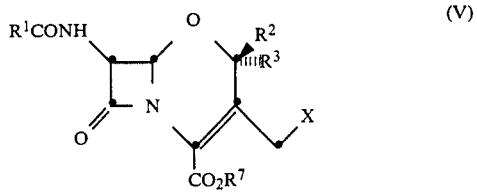

wherein $R^1$, $R^2$, $R_3$, $R^7$ and X are defined above, and reacting the resultant 7-N-acylated compound of the formula (V) with N-alkylpyrido-4-thion derivative of the formula (VI):

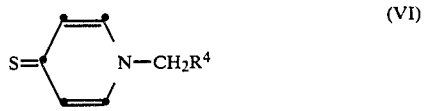

to give a compound of the general formula (VII):

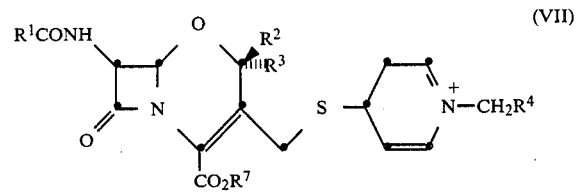

wherein $R^1$, $R^2$, $R^3$, $R^4$ and $R^7$ are as defined hereinabove, followed by removal in a conventional manner of the remaining protecting groups from the resultant compound of the formula (VII) above.

The steps in the process for the synthesis of the compound of the general formula (I) from the compound of the general formula (III) are described below.

In order to introduce a desired acyl group to the 7-amino group of the compound (III) is at first reacted with the carboxylic acid of the formula (IV) to effect the acylation on the 7-amino group, and thereby to obtain the 7-N-acylated product of the formula (V). This acylation reaction may be carried out in a conventional manner known per se.

The carboxylic acid of the formula (IV) may preferably be used in the form of a functional derivative of said carboxylic acid such as acid halide, an active acid ester, an acid anhydride or a mixed acid anhydride thereof. The acylation reaction may also be performed using the carboxylic acid of the formula (IV) which has not been activated as above, when the reaction may be carried out by a dehydration condensation method with carbodiimide or by a phosphorous oxychloride method. The acylation may generally be performed in an organic solvent which is inert to the reaction such as dioxane, tetrahydrofuran, dimethylformamide, methylene chloride, chloroform or ethyl dimethylformamide, methylene chloride, chloroform or ethyl acetate, at a temperature of $-50°$ C. to $+50°$ C.

Next, the 7-N-acylated product of the formula (V) is reacted with N-alkylprido-4-thion (VI) as the reagent to obtain the compound (VII). This replacement reaction at the 3'-position is itself a known reaction which is disclosed in the specification of Japanese patent application first publication "KOKAI" NO. 154980/80. The compounds (V) and (VI) are mixed with each other in an inert organic solvent, preferably in dimethylformanide (DMF), dimethylacetamide or dioxane, at $0°$ C. to $80°$ C. to effect the reaction. In the case of the compound of the formula (V) where X is a chlorine atom, 1-2 equivalent of sodium iodide (NaI) may preferably be added to the reaction system to ensure that the reaction proceeds in a higher yield.

The appropriate N-alkyl pyrido-4-thion for this reaction may be prepared according to the known procedure as described in "Journal of Chemical Society (London)", 3610 (1958), and Japanese Patent application "TOKUGAN" NO. 71414/84.

Removal of the remaining protecting group from the compound (VII) gives the compound of the general formula (I) according to this invention. The protecting groups which remaining in the compound (VII) are the carboxy-protecting group on the 4-carboxy group and the amino protecting group on the 2-amino group of the 2-aminothiazole side chain at the 7-position of the 1-oxacephem ring. These protecting groups may be removed successively or simultaneously in a conventional manner. In case $R^7$ is a diphenylmethyl group or p-nitrobenzyl group and 2-amino group of the 2-aminothiazole moiety has been protected with trityl group, these protecting groups are removed simultaneously by such a method as catalytic reduction or hydrolysis with an acidic reagent. The deprotection reaction for this purpose is known and performed in a conventional manner using an acidic reagents, for example, a mineral acid such as hydrochloric acid, an organic acid such as trifluoroacetic acid, or a Lewis acid such as aluminum chloride.

The compound of the general formula (III) employed as a starting material for this invention may be prepared according to U.S. patent application No. (695,333) dated Jan. 28, 1985 now abandoned or according to presently pending application Ser. No. 687,096 filed Dec. 28, 1984 which discloses the identical subject matter. by the present inventors by the following reaction flow sheet:

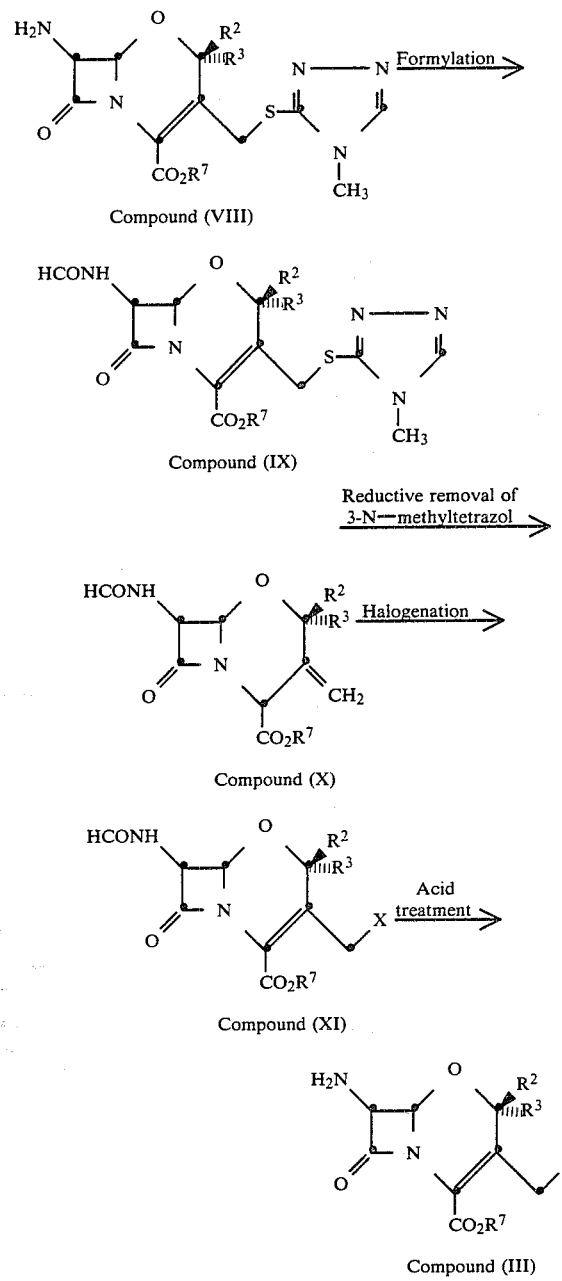

Compound (VIII)

Compound (IX)

Reductive removal of 3-N—methyltetrazol

Compound (X)

Compound (XI)

Compound (III)

In this reaction flow sheet, $R^2$, $R^3$, $R^7$ and X denote the same meaning as defined hereinbefore.

The compound of the formula (VIII) which is used as a starting material for the preparation of the compound (III) shown in the above reaction flow sheet and in which either one of $R^1$ and $R^2$ is a methyl group may be synthesized according to the method as disclosed in Japanese patent application first publications "KOKAI" NO. 46287/84 and NO. 51291/84 each invented by the present inventors. The compound (VIII) where $R^1$ and $R^2$ each is a hydrogen atom is a known compound which is disclosed in Japanese patent application First publications "KOKAI" NO. 3088/79 and NO. 2555/78. In these formulas in the reaction flow sheet shown above, $R^7$ is a carboxy-protecting group which may generally used for penicillins, cephalosporins and 1-oxa-1-dethiacephalo-sporins. These carboxy-protecting groups may preferably be an alkyl group such as t-butyl group, dichloroethyl group and trichloroethyl group; and an aralkyl group such as benzyl group, n-nitrobenzyl group, p-methpoxybenzyl group, phenacylmethyl group and diphenylmethyl group. Among these protecting groups, preferred are ones which are easily removed under a reductive condition, for example, diphenylmethyl group and p-nitrobenzyl group.

In the first step for the preparation of the compound (III), the starting compound (VIII) is formylated so that the 7-amino group is protected and the compound (IX) is formed. This formylation reaction may be carried out in a conventional manner, when it is convenient to use a mixture of formic acid and acetic anhydride or an active ester of formic acid, preferably trichlorophenyl ester of the formula:

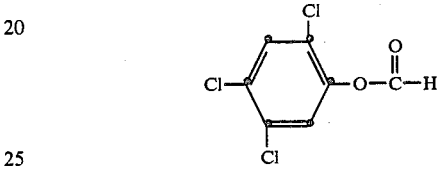

Thus, the 7-N-formylated product (IX) is obtained. Solvents used in the formylation may be an ordinary organic solvent, particularly an inert organic solvent which may preferably be methylene chloride, chloroform, tetrahydrofuran, dioxane and the like.

In the next 2nd step, the 3-N-methyltetrazole group of the compound (IX) is reductively removed to give the 3-methyleno-1-oxacepham compound of the formula (X). The reduction may be carried out at $-5°$ C. to 50° C. in an inert solvent in the presence of an organic, inorganic acid or Lewis acid as the hydrogen source and using a metal powder such as zinc, iron, magnesium and the like. The reduction is preferably performed in dimethylformamide, methylene chloride or dioxane using zinc or magnesium in the presence of formic acid or acetic acid. When the reaction is conducted with Lewis acid such as ammonium chloride, an addition of thiourea may make the reaction proceed in a higher yield.

In the 3rd step, the compound (X) is treated with a halogenating agent to give a corresponding 3-halogenomethyl compound (XI). Such compound of the formula (XI) where either of $R^2$ and $R^3$ is a methyl group is a novel compound, while usual cephalosporin compound and such compound of the formula (XI) where $R^2$ and $R^3$ each is a hydrogen atom are known compounds. The halogenation of the compounds (X) may be performed to the halogenation procedure as described in "Journal of American Chemical Society", Vol. 99, 2822 (1977) and "Tetrahedron", Vol. 39, NO. 15, 2512–2526 (1983). For the halogenation, the compound (X) may be reacted with bromine or iodine, preferably in the presence of organic base DBU to give a 3-bromomethyl compound (XI) (X=Br) or a 3-iodomethyl compound (XI) (X=I) respectively. A 3-chloromethyl compound (X=Cl) may be obtained by reacting the compound (X) with phenylselenyl chloride, followed by oxidative deselenylation of the resultant 3-phenylseleno-1-oxacepham compound.

In the 4th step, the formyl group for the 7-amino-protecting group of the compound (XI) is removed to give the compound of the formula (III). Deformylation by acid treatment is a well known reaction, and to this end anhydrous hydrochloric acid is preferred to ensure that the deformylation can be performed selectively without affecting the other protecting group which is present in the molecule and unstable to the acid, that is, the protecting group for the 4-carboxylic group of said compound (XI). The deformylation may be carried out with 2–8 equivalents of anhydous hydrochloric acid in an inert solvent at a temperature of −5° C. to +20° C. Depending on the procedure employed after the deformulation reaction, the compound of the general formula (III) is isolated either in the form of its free base or in the form of its hydrochloride.

Alternatively, a third aspect of this invention provides another synthetic procedure of the 1-oxa-1-dethiacephalosporins of the general formula (I), via 1-oxa-1-dethioacephalosporin compounds of the general formula (II):

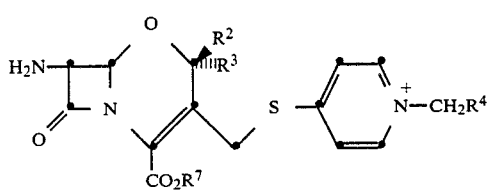

wherein R², R³, R⁴ and R⁷ are as defined above.

In an industrial preparation of 1-oxa-1-dethiacephalosporins of the general formula (I), there are many cases in which a few oxacephalosporins of the general formula (I) with one fixed R⁴ but with a few different R¹. For that cases the third aspect of this invention provides more practical methods, via 1-oxa-1-dethiacephalosporin compounds of the general formula (II) starting with 1-oxa-1-dethiacephalosporin compounds of the general formula (XI).

At first an appropriate 3'-substituent is introduced to a compound of the general formula (XI). The compound of the general formula (XI):

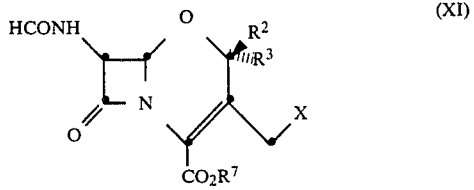

wherein R², R³, X and R⁷ are as defined herein above, is reacted with N-alkylpyrido-4-thion derivative of the formula (VI):

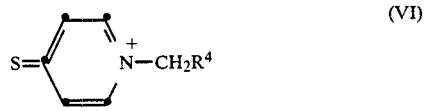

to give a compound of the general formula (XII):

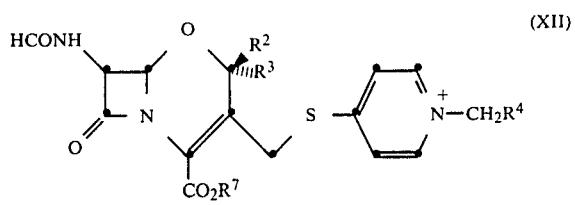

wherein R², R³, R⁴ and R⁷ are as defined hereinabove, followed by an acid treatment to deprotect formyl group on 7-amino group of the compound of the general formula (XII) to give a compound of the general formula (II). Finally the compound of the general (II) is acylated with a carboxylic acid of the general formula (IV) described above to give the compound of the general formula (VII) described above.

The compound (I) according to this invention is produced via the compound of the general formula (VII) according to the first aspect of this invention described above.

Reaction conditions to give compounds of general formula (XII and II) from the compound (XI) are basically as same as conditions used in the preparations according to the first aspects of this invention described above.

This invention is now illustrated with reference to the following Examples.

EXAMPLE 1

Preparation of (6R, 7R)-7-((Z)-2-(2-Aminothiazol-4-yl)-2-(2-carboxyprop-2-oxyimino)acetamide)-(2S)-2-methyl-3-(1-methylpyridinium-4-ylthiomethyl)-1-oxa-1-dethiaceph-3-em-4-carboxylate Sodium Salt Step (a): Diphenylmethyl (6R, 7R)-7-[(Z)-2-(2-Tritylaminothiazol-4-yl)-2-(2-diphenylmethoxycarbonylprop-2-oxyimino)acetamide]-(2S)-2-methyl-3-chloromethyl-1-oxa-1-dethiaceph-3-em-4-carboxylate Pyridine (0.26 ml, 3.2 mmol) and phosphorous oxychloride (0.08 ml, 0.9 mmol) were added to a mixture of diphenylmethyl (6R, 7R)-7-amino-(2S)-2-methyl-3-chloromethyl-1-oxa-1-dethiaceph-3-em-4-carboxylate HCl salt (360 mg, 0.8 mmol) and (Z)-2-(2-tritylaminothiazol-4-yl)-2-(2-diphenylemethoxycarbonylprop-2-oxyimino)acetic acid (610 mg, 0.9 mmol) in 8.0 ml of dichloromethane at 0°–5° C. The mixture was stirred at the same temperature for 10 minutes, then diluted with 7.0 ml of chloroform, washed with water, dried over magnesium sulfate, and evaporated under vacuum. The residue was chromatographed on silica gel (benzene-ethyl acetate=20:1) to give 645 mg of diphenylmethyl (6R, 7R)-7-[(Z)-2-(2-tritylamino-thiazol]-4-yl)-2-(2-diphenylmethoxycarbonyprop-2-oxyimino)acetamide]-(2S)-2-methyl-3-chloromethyl-1-oxa-1-dethiaceph-3-em-4-carboxylate.

NMR (CDCl₃) δ(ppm): 1.13 (3H, d, J=7.6 Hz), 1.65 (3H, s), 1.69 (3H, s), 3.98, 5.15 (2H, ABq, J=14.7 Hz), 4.63 (1H, q, J=7.6 Hz), 5.07 (1H, d, J=3.9 Hz), 5.83 (1H, dd, J=3.9, 9.6 Hz), 6.67 (1H, s), 6.81 (1H, s), 6.87 (1H, s), 7.1–7.6 (36H, m).

Step (b): Diphenylmethyl (6R, 7R)-7-[(Z)-2-(2-T ritylaminothiazol-4-yl)-2-(2-diphenylmethoxycarbonylprop-2-oxyimino)acetamide]-(2S)-2-methyl-3-(1-methylpyridinium-4-ylthiomethyl)-1-oxa-1-dethiaceph-3-em-4-carboxylate Iodide 1-Methyl-4-thiopyridone (70 mg, 0.56 mmol) and NaI (150 mg, 1.0 mmol) were added to a solution of the product from the step (a) (600 mg, 0.56 mmol) in 6.0 ml of N,N-dimethylformamide, and the mixture was stirred at room temperature for 15 minutes. The resulting mixture was diluted with 30 ml of ethyl acetate and 30 ml of chloroform, washed with water and 1N hydrochloric acid and water successively, and dried over magnesium sulfate. Removal of solvents in vacuo gave 700 mg of crude diphenylmethyl (6R, 7R)-7-[(Z)-2-(2-tritylamino thiazol-4-yl)-2-(2-diphenylmethoxy-carbonylprop-2-oxyimino)acetamide]-(2S)-2-methyl-3-(1-methyl-pyridinium-4-ylthiomethyl)-1-oxa-1-dethiaceph-3-em-4-carboxylate iodide which was used to the next step without further purification.

Step (c): (6R, 7R)-7-[(Z)-2-(2-Aminothiazol-4-yl)-2-(2-carboxyprop-2-oxyimino)acetamide]-(2S)-2-methyl-3-(1-methylpyridinium-4-ylthiomethyl)-1-oxa-1-dethiaceph-3-em-4-carboxylate Sodium Salt Trifluoroacetic acid (7.0 ml) was added to a mixture of the product (700 mg) from the step (b) and anisole (2.1 ml) at 0°-5° C., and the resulting solution was stirred at the same temperature for 40 minutes. Diisopropyl ether was added to the stirring mixture to give a precipitate.

The precipitate (410 mg) collected by filtration was dissolved in 5.0 ml of water with sodium bicarbonate and purified by column chromatography on Diaion HP-20 (methanol-water=1:4) to give 230 mg of (6R, 7R)-7-[(Z)-2-(2-aminothiazol-4-yl)-2-(2-carboxyprop-2-oxyimino)acetamide]-(2S)-2-methyl-3-(1-methyl-pyridinium-4-ylthiomethyl)-1-oxa-1-dethiaceph-3-em-4-carboxylate sodium salt.

NMR ($D_2O$) (ppm): 1.45 (3H, s), 1.47 (3H, s), 1.49 (3H, d, J=7.0 Hz), 4.19 (3H, s), 4.75 (1H, q, J=3.5 Hz), 5.58 (1H, d, J=3.5 Hz), 7.00 (1H, s), 7.00, 8.40 (4H, ABq, J=6.2 Hz).

EXAMPLE 2

Preparation of (6R, 7R)-7-[(Z)-2-(2-Aminothiazol-4-yl)-2-(2-carboxyprop-2-oxyimino)acetamide]-(2S)-2-methyl-3-(1-ethyl-pyridinium-4-ylthiomethyl)-1-oxa-1-dethiaceph-3-em-4-carboxylate Sodium Salt Step (a): Diphenylmethyl (6R, 7R)-7-[(Z)-2-(2-Tritylaminothiazol-4-yl)-2-(2-diphenylmethoxycarbonylprop-2-oxyimino)acetamide]-(2S)-2-methyl-3-(1-ethylpyridinium-4-ylthiomethyl)-1-oxa-1-dethiaceph-3-em-4-carboxylate Iodide 1-Ethyl-4-thiopyridone (12.5 mg, 0.09 mmol) and NaI (30 mg, 0.2 mmol) were added to a solution of diphenylmethyl (6R, 7R)-7-[(Z)-2-tritylaminothiazol-4-yl)-2-(2-diphenylmethoxycarbonylprop-2-oxyimino)acetamide]-(2S)-2-methyl-3-chloromethyl-1-oxa-1-dethiaceph-3-em-4-carboxylate prepared in the step (a) of Example 1 in 0.86 ml of N,N-dimethylformamide, and the mixture was stirred at room temperature for 15 minutes.

The resulting mixture was diluted with 4.3 ml of ethyl acetate and 4.3 ml of chloroform, washed with water and 1N hydrochloric acid and water successively, and dried over magnesium sulfate. Removal of solvents in vacuo gave 100 mg of crude diphenylmethyl (6R, 7R)-7-[(Z)-2-tritylaminothiazol-4-yl)-2-(2-diphenylmethoxycarbonylprop-2-oxyimino)acetamide]-(2S)-2-methyl-3-(1-ethyl-pyridinium-4-ylthiomethyl)-1-oxa-1-dethiaceph-3-em-4-carboxylate iodide which was used to the next step without further purification.

Step (b): (6R, 7R)-7-[(Z)-2-(2-Aminothiazol-4-yl)-2-(2-carboxyprop-2-oxyimino)acetamide]-(2S)-2-methyl-3-(1-ethylpyridinium-4-ylthiomethyl)-1-oxa-1-dethiaceph-3-em-4-carboxylate Sodium Salt Trifluoroacetic acid (1.0 ml) was added to a mixture of the product (100 mg) from the step (a) and anisole (0.3 ml) at 0°-5° C., and the resulting solution was stirred at the same temperature for 40 minutes.

Diisopropyl ether was added to the stirring mixture to give a precipitate.

The precipitate (46 mg) collected by filtration was dissolved in 1.0 ml of water with sodium bicarbonate and purified by column chromatography on Diaion HP-20 (methanol-water=1:4) to give 30 mg of (6R, 7R)-7-[(Z)-2-(2-aminothiazol-4-yl)-2-(2-carboxyprop-2-oxyimino)acetamide]-(2S)-2-methyl-3-(1-ethylpyridinium-4-yl-thiomethyl)-1-oxa-1-dethiaceph-3-em-4-carboxylate sodium salt.

NMR ($D_2O$) (ppm): 1.50–1.70 (12H), 3.90–5.00 (5H), 5.30 (1H, d, J=4 Hz), 5.67 (1H, d, J=4 Hz), 7.10 (1H, s), 7.80, 8.55 (4H, ABq, J=8 Hz).

EXAMPLE 3

Preparation of (6R, 7R)-7-[(Z)-2-(2-Aminothiazol-4-yl)-2-(2-carboxyprop-2-oxyimino)acetamide]-(2S)-2-methyl-3-[1-(2-fluoroethyl)pyridinium-4-ylthiomethyl]-1-oxa-1-dethiaceph-3-em-4-carboxylate Sodium Salt Step (a): Diphenylmethyl (6R, 7R)-7-[(Z)-2-Tri tylaminothiazol-4-yl)-2-(2-diphenylmethoxycarbonylprop-2-oxyimino)acetamide]-(2S)-2-methyl-3-[1-(2-fluoroethyl)pyridinium-4-ylthiomethyl]-1-oxa-1-dethiaceph-3-em-4-carboxylate Iodide 1-(2-Fluoroethyl)-4-thiopyridone (13 mg, 0.08 mmol) and NaI (30 mg, 0.2 mmol) were added to a solution of diphenylmethyl (6R, 7R)-7-[(Z)-2-tritylaminothiazol-4-yl)-2-(2-diphenylmethoxycarbonylprop-2-oxyimino)acetamide]-(2S)-2-methyl-3-chloromethyl-1-oxa-1-dethiaceph-3-em-4-carboxylate (85 mg, 0.08 mmol) prepared in the step (a) of Example 1 in 0.86 ml of N,N-dimethylformamide, and the mixture was stirred at room temperature for 15 minutes. The resulting mixture was diluted with 4.3 ml of ethyl acetate, washed with water and 1N hydrochloric acid and water successively, and dried over magnesium sulfate.

Removal of solvents in vacuo gave 95 mg of crude diphenylmethyl (6R, 7R)-7-[(Z)-2-(2-tritylaminothiazol-4-yl)-2-(2-diphenylmethoxy-carbonylprop-2-oxyimino)acetamide]-(2S)-2-methyl-3-[1-(2-fluoroethyl)pyridinium-4-ylthiomethyl]-1-oxa-1-dethiaceph-3-em-4-carboxylate iodide which was used to the next step without further purification.

Step (b): (6R, 7R)-7-[(Z)-2-(2-Aminothiazol-4-yl)-2-(2-carboxyprop-2-oxyimino)acetamide]-(2S)-2-methyl-3-[1-(2-fluoroethyl)pyridinium-4-ylthiomethyl]-1-oxa-1-dethiaceph-3-em-4-carboxylate Sodium Salt Trifluoroacetic acid (0.95 ml) was added to a mixture of the product (95 mg) from the step (a) and anisole (0.3 ml) at 0°-5° C., and the resulting solution was stirred at the same temperature for 40 minutes.

Diisopropyl ether was added to the stirring mixture to give a precipitate.

The precipitate (50 mg) collected by filtration was dissolved in 1.0 ml of water with sodium bicarbonate and purified by column chromatography on Diaion HP-20 (methanol-water=1:4) to give 30 mg of (6R, 7R)-7-[(Z)-2-aminothiazol-4-yl)-2-(2-carboxyprop-2- oxyimino)acetamide]-(2S)-2-methyl-3-[1-(2-fluoroethyl)pyridinium-4-ylthiomethyl]-1-oxa-1-dethiaceph-3-em-4-carboxylate sodium salt.

NMR (D$_2$O) δ(ppm): 1.56 (9H), 3.90–5.20 (7H), 5.30 (1H, d, J=4 Hz), 5.65 (1H, d, J=4 Hz), 7.05 (1H, s), 7.83, 8.55 (4H, ABq, J=8 Hz).

EXAMPLE 4

Preparation of (6R, 7R)-7-[(Z)-2-(2-Aminothiazol-4-yl)-2-(2-carboxyprop-2-oxyimino)acetamide]-(2S)-2-methyl-3-[1-(2,2,2-trifluoroethyl)pyridinium-4-ylthiomethyl]-1-oxa-1-dethiaceph-3-em-4-carboxylate Sodium Salt Step (a): Diphenylmethyl (6R, 7R)-7-[(Z)-2-Tritylaminothiazol-4-yl)-2-(2-diphenylmethoxycarbonylprop-2-oxyimino)acetamide]-(2S)-2-methyl-3-[1-(2,2,2-trifluoroethyl)pyridinium-4-ylthiomethyl]-1-oxa-1-dethiaceph-3-em-4-carboxylate Iodide 1-(2,2,2-Trifluoroethyl)-4-thiopyridone (17 mg, 0.09 mmol) and NaI (23 mg, 0.16 mmol) were added to a solution of diphenylmethyl (6R, 7R)-7-[(Z)-2-tritylaminothiazol-4-yl)-2-(2-diphenylmethoxycarbonylprop-2-oxyimino)acetamide]-(2S)-2-methyl-3-chloromethyl-1-oxa-1-dethiaceph-3-em-4-carboxylate (86 mg, 0.08 mmol) prepared in the step (a) of Example 1 in 0.86 ml of N,N-dimethylformamide, and the mixture was stirred at room temperature for 15 minutes. The resulting mixture was diluted with 4.3 ml of ethyl acetate, washed with water and 1N hydrochloric acid and water successively, and dried over magnesium sulfate.

Removal of solvents in vacuo gave 97 mg of crude diphenylmethyl (6R, 7R)-7-[(Z)-2-tritylaminotiazol-4-yl)-2-(2-diphenylmethoxycarbonylprop-2-oxyimino)acetamide]-(2S)-2-methyl-3-[1-(2,2,2-trifluoroethyl)pyridinium-4-ylthiomethyl]-1-oxa-1-dethiaceph-3-em-4 -carboxylate iodide which was used to the next step without further purification.

Step (b): (6R, 7R)-7-[(Z)-2-(2-Aminothiazol-4-yl)-2-(2-carboxyprop-2-oxyimino)acetamide]-(2S)-2-methyl-3-[1-(2,2,2-trifluorethyl)-pyridinium-4-ylthiomethyl]-1-oxa-1-dethiaceph-3-em-4-carboxylate Sodium Salt Trifluoroacetic acid (0.97 ml) was added to a mixture of the product (97 mg) from the step (a) and anisole (0.3 ml) at 0°–5° C., and the resulting solution was stirred at the same temperature for 40 minutes.

Diisopropyl ether was added to the stirring mixture to give a precipitate.

The precipitate (54 mg) collected by filtration was dissolved in 1.0 ml of water with sodium bicarbonate and purified by column chromatography on Diaion HP-20 (methanol-water=1:4) to give 27 mg of (6R, 7R)-7-[(Z)-2-(2-aminothiazol-4-yl)-2-(2-carboxyprop-2-oxyimino)acetamide]-(2S)-2-methyl-3-[1-(2-fluoroethyl)pyridinium-4-ylthiomethyl]-1-oxa-1-dethiaceph-3-em-4-carboxylate sodium salt.

NMR (D$_2$O) δ(ppm): 1.55 (9H), 4.46 (2H), 4.85 (1H, q, J=8 Hz), 5.27 (1H, d; J=4 Hz), 5.30, 5.45 (2H, ABq, J=12 Hz), 5.65 (1H, d, J=4 Hz), 7.05 (1H, s), 7.86, 8.63 (4H, ABq, J=8 Hz).

EXAMPLE 5

Preparation of (6R, 7R)-7-[(Z)-2-(2-Aminothiazol-4-yl)-2-(2-carboxyprop-2-oxyimino)acetamide]-(2S)-2-methyl-3-(1-carboxymethylpyridinium-4-ylthiomethyl)-1-oxa-1-dethiaceph-3-em-4-carboxylate Sodium Salt Step (a): Diphenylmethyl (6R, 7R)-7-[(Z)-2-(2-Tritylaminothiazol-4-yl)-2-(2-diphenylmethoxy-carbonylprop-2-oxyimino)acetamide]-(2S)-2-methyl-3-(1-diphenylmethoxycarbonylmethylpyridinium-4-ylthiomethyl)-1-oxa-1-dethiaceph-3-em-4-carboxylate Iodide 1-Diphenylmethoxycarbonylmethyl-4-thiopyridone (37 mg, 0.11 mmol) and NaI (30 mg, 0.2 mmol) were added to a solution of diphenylmethyl (6R, 7R)-7-[(Z)-2-tritylaminothiazol-4-yl)-2-(2-diphenylmethoxycarbonylprop-2-oxyimino)acetamide]-(2S)-2-methyl-3-chloromethyl-1-oxa-1-dethiaceph-3-em-4-carboxylate (108 mg, 0.10 mmol) prepared in the step (a) of Example 1 in 1.1 ml of N,N-dimethylformamide, and the mixture was stirred at room temperature for 15 minutes.

The resulting mixture was diluted with 5.4 ml ethyl acetate, washed with water and 1N hydrochloric acid and water successively, and dried over magnesium sulfate.

Removal of solvents in vacuo gave 150 mg of crude diphenylmethyl (6R, 7R)-7-[(Z)-2-(2-tritylaminothiazol-4-yl)-2-(2-diphenylmethoxy-carbonylprop-2-oxyimino)acetamide]-(2S)-2-methyl-3-(1-diphenylmethoxycarboxymethylpyridinium-4-ylthiomethyl)-1-oxa-1-dethiaceph-3-em-4-carboxylate iodide which was used to the next step without further purification.

Step (b): (6R, 7R)-7-[(Z)-2-(2aminothiazol-4-yl)-2-(2-carboxyprop-2-oxyimino)acetamide]-(2S)-2-methyl-3-(1-carboxymethylpyridinium-4-ylthiomethyl)-1-oxa-1-dethiaceph-3-em-4-carboxylate Sodium Salt Trifluoroacetic acid (1.5 ml) was added to a mixture of the product (150 mg) from the step (a) and anisole (0.45 ml) at 0°–5° C., and the resulting solution was stirred at the same temperature for 40 minutes.

Diisopropyl ether was added to the stirring mixture to give a precipitate.

The precipitate (60 mg) collected by filtration was dissolved in 1.0 ml of water with sodium bicarbonate and purified by column chromatography on Diaion HP-20 (water) to give 36 mg of (6R, 7R)-7-[(Z)-2-(2-aminothiazol-4-yl)-2-(2-carboxyprop-2-oxyimino)acetamide]-(2S)-2-methyl-3-(1-carboxymethylpyridinium-4-ylthiomethyl)-1-oxa-1-dethiaceph-3-em-4-carboxylate sodium salt.

NMR (D$_2$O) δ(ppm): 1.50 (9H), 4.40 (2H), 4.80 (1H, q, J=8 Hz), 5.05 (2H s), 5.23 (1H, d, J=4 Hz), 5.60 (1H, d, J=4 Hz), 7.00 (1H, s), 7.73, 8.37 (4H, ABq, J=8 Hz).

EXAMPLE 6

Preparation of (6R, 7R)-7-[(Z)-2-(2Aminothiazol-4-yl)-2-methoxyiminoacetamide]-(2S)-methyl-3-[1-(2,2,2-trifluoroethyl)pyridinium-4-ylthiomethyl]-1-oxa-1-dethiaceph-3-em-4-carboxylate Step (a): Diphenylmethyl (6R, 7R)-7-[(Z)-2-(2-Tritylaminothiazol-4-yl)-2-(methoxyiminoacetamide]-(2S)-2-methyl-3-[1-(2,2,2-trifluoroethyl)-pyridinium-4-ylthiomethyl]-1-oxa-1-dethiaceph-3-em-4-carboxylate Iodide 1-(2,2,2-Trifluoroethyl)-4-thiopyridone (18 mg, 0.11 mmol) and NaI (30 mg, 0.2 mmol) were added to a solution of diphenylmethyl (6R, 7R)-7-[(Z)-2-tritylaminothiazol-4-yl)-2-methoxyiminoacetamide]-(2S)-2-methyl-3-chloromethyl-1-oxa-1-dethiaceph-3-em-4-carboxylate (89 mg, 0.1 mmol), which was prepared in the similar manner as in the step (a) of Example 1 using (Z)-2-(2-tritylaminothiazol-4-yl)-2-methoxyiminoacetic acid instead of (Z)-2-(2-tritylaminothiazol-4-yl)-2-(2-diphenylmethoxycarbonylprop-2-oxyimino)acetic acid, in 0.9 ml of N,N-diphenylformamide. The mixture was stirred at room temperature for 15 minutes, then diluted with 4.5 ml of ethyl acetate, washed with water and 1N hydrochloric acid and water successively, and dried over magnesium sulfate.

Removal of solvents in vacuo gave 105 mg of crude diphenylmethyl (6R, 7R)-7-[(Z)-2-(2-tritylaminothiazol-4-yl)-2-methoxyiminoacetamide]-(2S)-2-methyl-3-[1-(2,2,2-trifluoroethyl)pyridinium-4-ylthiomethyl]-1-oxa-1-dethiaceph-3-em-4-carboxylate iodide.

Step (b): Preparation of (6R, 7R)-7-[(Z)-2-(2-Aminothiazol-4-yl)-2-methoxyiminoacetamide]-(2S)-2-methyl-3-[1-(2,2,2-trifluoroethyl)pyridinium-4-ylthiomethyl]-1-oxa-1-dethiaceph-3-em-4-carboxylate Trifluoroacetic acid (1.05 ml) was added to a mixture of the product (105 mg) from the step (a) and anisole (0.32 ml) at 0.5° C., and the mixture was stirred at the same temperature for 40 minutes. Diisopropyl ether was added to the stirring mixture to give a precipitate.

The precipitate (86 mg) collected by filtration was dissolved in 1.0 ml of water with sodium bicarbonate and purified by column chromatography on Diaion HP-20 (methanol-water=1:1) to give 55 mg of (6R, 7R)-7-[(Z)-2-(2-aminothiazol-4-yl)-2-methoxyiminoacetamide]-(2S)-2-methyl-3-(1-(2,2,2-trifluoroethyl)pyridinium-4-ylthiomethyl-1-oxa-1-dethiaceph-3-em-4-carboxylate.

NMR (D$_2$O) δ(ppm): 1.48 (3H, d, J=6.7 z), 3.96 (3H, s), 4.74 (1H, q, J=6.7 Hz), 4.85 (2H), 5.20 (1H, d, J=3.5 Hz), 5.31 (2h, s), (5.52 (1H, d, J=3.5 Hz), 7.04 (1H, s), 7.83, 8.56 (4H, ABq, J=7.0 Hz).

EXAMPLE 7

Preparation of (6R, 7R)-7-[(Z)-2-(2-Aminothiazol-4-yl)-2-methoxyiminoacetamide]-(2S)-2-methyl-3-[1-carboxymethylpyridinium-4-ylthiomethyl]-1-oxa-1-dethiaceph-3-em-4-carboxylate Sodium Salt Step (a): Diphenylmethyl (6R, 7R)-7-[(Z)-2-(2-Tritylaminothiazol4-yl)-2-methoxyiminoacetamide]-(2S)-2-methyl-3-[1-diphenylmethoxycarbonylmethylpyridinium-4-ylthiomethyl]-1-oxa-1-dethiaceph-3-em-4-carboxylate Iodide 1-Diphenymethoxycarbonylmethyl-4-thiopyridone (30 mg, 0.09 mmol) and NaI (30 mg, 0.2 mmol) were added to a solution of diphenylmethyl (6R, 7R)-7-[(Z)-2-(tritylaminothiazol-4-yl)-2-methoxyiminoacetamide]-(2S)-2-methyl-3-chloromethyl-1-oxa-1-dethiaceph-3-em-4-carboxylate (89 mg, 0.1 mmol) which was prepared in the step (a) of Example 6 in 0.76 ml of N,N-dimethylformamide.

The mixture was stirred at room temperature for 15 minutes, then diluted with 3.8 ml of ethyl acetate, washed with water and 1N hydrochloric acid and water successively, and dried over magnesium sulfate.

Removal of solvents in vacuo gave 93 mg of crude diphenylmethyl (6R, 7R)-7-[(Z)-2-(2-tritylaminothiazol-4-yl)-2-methoxyiminoacethamide]-(2S)-2-methyl-3-[1-diphenylmethoxycarbonymethylpyridinium-4-ylthiomethyl]-1-oxa-1-dethiaceph-3-em-4-carboxylate iodide.

Step (b): Preparation of (6R, 7R)-7-[(Z)-2-(2-Aminothiazol-4-yl)-2-methoxyiminoacetamide]-(2S)-2-methyl-3-[1-carboxymethylpyridinium-4-ylthiomethyl]-1-oxa-1-dethiaceph-3-em-4-carboxylate Sodium Salt Trifluoroacetic acid (0.93 ml) was added to a mixture of the product (93 mg) from step (a) and anisole (0.28 ml) at 0°-5° C., and the mixture was stirred at the same temperature for 40 minutes.

Diisopropyl ether was added to the stirring mixture to give a precipitate.

The precipitate (66 mg) collected by filtration was dissolved in 1.0 ml of water with sodium bicarbonate and purified by column chromatography on Diaion HP-20 (methanol-water=1:4) to give 30 mg of (6R, 7R)-7-[(Z)-2-(2-Aminothiazol-4-yl)-2-methoxyiminoacetamide]-(2S)-2-methyl-3-(1-carboxymethylpyridinium-4-ylthiomethyl)-1-oxa-1-dethiaceph-3-em-4-carboxylate sodium salt.

NMR (D$_2$O) δ(ppm): 1.60 (3H, d, J=7 Hz), 4.06 (3H, s), 4.74 (1H, q, J=7 Hz), 4.85 (2H), 5.13 (2H, s), 5.30 (1H, d, J=4 Hz), 5.63 (1H, d, J=4 Hz), 7.10 (1H, s), 7.80, 8.45 (4H, ABq, J=8 Hz).

EXAMPLE 8

Preparation of (6R, 7R)-7-[(Z)-2-(2-Aminothiazol-4-yl)-2-ethoxyiminoacetamide]-(2S)-2-methyl-3-(1-carboxymethylpyridinium-4-ylthiomethyl)-1-oxa-1-dethiaceph-3-em-4-carboxylate Sodium Salt Step (a) Diphenylmethyl (6R, 7R)-7-[(Z)-2-Tritylaminothiazol-4-yl)-2-ethoxyiminoacetamide]-(2S)-2-methyl-3-[1-diphenylmethoxycarbonylmethylpyridinium-4-ylthiomethyl]-1-oxa-1-dethiaceph-3-em-4-carboxylate Iodide 1-Diphenymethoxycarbonylmethyl-4-thiopyridone (37 mg, 0.11 mmol) and NaI (30 mg, 0.2 mmol) were added to a solution of diphenylmethyl (6R, 7R)-7-[(Z)-2-(2-tritylaminothiazol-4-yl)-2-ethoxyiminoactamide]-(2S)-2-methyl-3-chloromethyl-1-oxa-1-dethiaceph-3-em-4-carboxylate (85 mg, 0.1 mmol), which was prepared in the similar manner as in the step (a) of Example 1 using (Z)-2-(2-tritylaminothiazol-4-yl)-2-ethoxyiminoacetic acid instead of (Z)-2-(2-tritylaminothiazol-4-yl)-2-(diphenylmethoxycarbonylprop-2-oxyimino)acetic acid, in 0.85 ml of N,N-dimethylformamide.

The mixture was stirred at room temperature for 15 minutes, then diluted with 4.3 ml of ethyl acetate, washed with water and 1N hydrochloric acid and water successively, and dried over magnesium sulfate.

Removal of solvents in vacuo gave 115 mg of crude diphenylmethyl (6R, 7R)-7-[(Z)-2-(2-tritylaminothiazol-4-yl)-2-ethoxyiminoacetamide]-(2S)-2-methyl-3-[1-diphenylmethoxycarbonylmethylpyridinium-4-ylthiomethyl]-1-oxa-1-dethiaceph-3-em-4-carboxylate iodide.

Step (b): Preparation of (6R, 7R)-7-[(Z)-2-(2-Aminothiazol-4-yl)-2-ethoxyiminoacetamide]-(2S)-2-methyl-3-(1-carboxymethylpyridinium-4-ylthiomethyl)-1-oxa-1-dethiaceph-3-em-4-carboxylate Sodium Salt Trifluoroacetic acid (1.15 ml) was added to a mixture of the product (115 mg) from step (a) and anisole (0.35 ml) at 0°-5° C., and the mixture was stirred at the same temperature for 40 minutes.

Diisopropyl ether was added to the stirring mixture to give a precipitate.

The precipitate (72 mg) collected by filtration was dissolved in 1.0 ml of water with sodium bicarbonate and purified by column chromatography on Diaion HP-20 (methanol-water=1:4) to give 30 mg of (6R, 7R)-7-[(Z)-2-(2-aminothiazol-4-yl)-2-ethoxyiminoacetamide]-(2S)-2-methyl-3-(1-carboxymethylpyridinium-4-ylthiomethyl)-1-oxa-1-dethiaceph-3-em-4-carboxylate sodium salt.

NMR (D$_2$O) δ(ppm): 1.35 (3H, t, J=8 Hz), 1.55 (3H, t, J=8 Hz), 4.30 (2H, q, J=8 Hz), 4.70 (1H, q, J=8 Hz), 4.85 (2H), 5.10 (2H, s), 5.23 (1H, d, J=4 Hz), 5.60 (1H, d, J=4 Hz), 7.06 (1H, s), 7.76, 8.45 (4H, ABq, J=9 Hz).

EXAMPLE 9

Preparation of (6R, 7R)-7-((Z)-2-(2-Aminothiazol-4-yl)-2-carboxymethoxyiminoacetamide)-(2S)-2-methyl-3-(1-carboxymethylpyridinium-4-yl-thiomethyl)-1-oxa-1-dethiaceph-3-em-4-carboxylate Sodium Salt Step (a): Diphenylmethyl (6R,7R)-7-((Z)-2-(2-Trityl aminothiazol-4-yl)-2-diphenylmethoxycarbonylmethoxyiminoacetamide)-(2S)-2-methyl-3-(1-diphenylmethoxycarbonylmethylpyridinium-4-yl-thiomethyl)-1-oxa-1-dethiaceph-3-em-4-carboxylate Iodide 1-Diphenylmethoxycarbonylmethyl-4-thiopyridone (34 mg, 0.1 mmol) and NaI (30 mg, 0.2 mmol) were added to a solution of diphenylmethyl (6R,7R)-7-((Z)-2-(2-tritylaminothiazol-4-yl)-2-diphenylmethoxycarbonylmethoxyiminoacetamide)-(2S)-2-methyl-3-chloromethyl-1-oxa-1-dethiaceph-3-em-4-carboxylate (103 mg, 0.1 mmol), which was prepared in the similar manner as in the step (a) of Example 1 using (Z)-2-(2-tritylaminothiazol-4-yl)-2-diphenylmethoxycarbonylmethoxyiminoacetic acid instead of (Z)-2-(2-tritylaminothiazol-4-yl)-2-(1-diphenylmethoxycarbonylprop-2-oxyimino)acetic acid, in 1.0 ml of N,N-dimethylformamide.

The mixture was stirred at room temperature for 15 minutes, then diluted with 5.2 ml of ethyl acetate, washed with water and 1N hydrochloric acid and water successively, and dried over magnesium sulfate.

Removal of solvent in vacuo gave 110 mg of crude diphenylmethyl (6R,7R)-7-((Z)-2-(2-tritylaminothiazol-4-yl)-2-diphenylmethoxycarbonylmethoxyiminoacetamide)-(2S)-2-methyl-3-(1-diphenylmethoxycarbonylmethylpyridinium-4-yl-thiomethyl)-1-oxa-1-dethiaceph-3-em-4-carboxylate iodide.

Step (b): Preparation of (6R,7R)-7-((Z)-2-(2-Aminothiazol-4-yl)-2-carboxymethoxyiminoacetamide)-(2S)-2-methyl-3-(1-carboxymethylpyridinium-4-yl-thiomethyl)-1-oxa-1-dethiaceph-3-em-4-carboxylate Sodium Salt Trifluoroacetic acid (1.1 ml) was added to a mixture of the product (110 mg) from the step (a) and anisole (0.35 ml) at 0°-5° C., and the mixture was stirred at the same temperature for 40 minutes.

Diisopropyl ether was added to the stirring mixture to give a precipitate.

The precipitate (65 mg) collected by filtration was dissolved in 1.0 ml of water with sodium bicarbonate and purified by column chromatography on Diaion HP-20 (water) to give 30 mg of (6R,7R)-7-((Z)-2-(2-aminothiazol-4-yl)-2-carboxymethoxyiminoacetamide)-(2S)-2-methyl-3-(1-carboxymethylpyridinium-4-ylthiomethyl)-1-oxa-1-dethiaceph-3-em-4-carboxylate sodium salt.

NMR (D$_2$O) δ (ppm): 150 (3H, d, J=8 z), 4.60 (2H, s), 4.70 (1H, q, J=8 Hz), 4.85 (2H), 5.05 (2H, s), 5.23 (1H, d, J=4 Hz), 5.56 (1H, d, J=4 Hz), 7.05 (1H, s), 7.75, 8.37 (4H, ABq, J=8 Hz).

EXAMPLE 10

Preparation of (6R,7R)-7-((Z)-2-(2-Aminothiazol-4-yl)-2-methoxyiminoacetamide)-3-(1-methylpyridinium-4-ylthiomethyl)-1-oxa-1-dethiaceph-3-em-4-carboxylate Step (a): Diphenylmethyl (6R,7R)-7-((Z)-2-(Tritylaminothiazol-4-yl)-2-methyloxyiminoacetamide)-3-chloromethyl-1-oxa-1-dethiaceph-3-em-4-carboxylate Pyridine (0.1 ml, 1.25 mmol) and phosphorous oxychloride (0.027 ml, 0.3 mmol) were added to a mixture of diphenylmethyl (6R,7R)-7-amino-3-chloromethyl-1-oxa-1-dethiaceph-3-em-4-carboxylate HCl salt (110 mg, 0.25 mmol) and (Z)-2-(2-tritylaminothiazol-4-yl)-2-methoxyiminoacetic acid (133 mg, 0.3 mmol) in 2.5 ml of dichloromethane at 0°-5° C., and the mixture was stirred at the same temperature for 10 minutes.

The resulting mixture was diluted with 10 ml of chloroform, washed with water (5 ml×2), dried over magnesium sulfate, and evaporated under vacuum.

The residue was chromatographed on silica gel (benzene-ethyl acetate=7:1) to give 165 mg (80%) of diphenylmethyl (6R,7R)-7-((Z)-2-(2-tritylaminothiazol-4-yl)-2-methoxyiminoacetamide)-3-chloromethyl-1-oxa-1-dethiaceph-3-em-4-carboxylate.

NMR (CDCl$_3$) (ppm): 4.05 (3H, s), 4.54 (4H, s), 5.12 (1H, d, J=3.8 Hz), 5.77 (1H, dd, J=3.8, 9.3 Hz), 6.76 (1H, s), 6.91 (1H, s), 7.10–7.60 (27H, m).

Step (b): Diphenylmethyl (6R,7R)-7-((Z)-2-(2-tritylaminothiazol-4-yl)-2-methoxyiminoacetamide)-3-(1-methylpyridinium-4-ylthiomethyl)-1-oxa-1-dethiaceph-3-em-4-carboxylate Iodide 1-Methyl-4-thiopyridone (25 mg, 0.2 mmol) and NaI (60 mg, 0.4 mmol) were added to a solution of the product (165 mg, 0.2 mmol) from the step (a) in 1.6 ml of N,N-dimethylformamide, and the mixture was stirred at room temperature for 30 minutes.

The resulting mixture was diluted with 8.3 ml of ethyl acetate and 8.3 ml of chloroform, washed with water and 1N hydrochloric acid and water successively, and dried over magnesium sulfate. Removal of solvents in vacuo gave a crude diphenylmethyl (6R,7R)-7-((Z)-2-(tritylaminothiazol-4-yl)-2-methoxyiminoacetamide)-3-(1-methylpyridinium-4-ylthiomethyl)-1-oxa-1-dethiaceph-3-em-4-carboxylate iodide.

Step (c): (6R,7R)-7-((Z)-2-(2-Aminothiazol-4-yl)-2-methoxyiminoacetamide)-3-(1-methylpyridinium-4-ylthiomethyl)-1-oxa-1-dethiaceph-3-em-4-carboxylate Trifluoroacetic acid (2.0 ml) was added to a mixture of the product (200 mg) from the step (b) and anisole (0.6 ml) at 0°-5° C., and the resulting solution was stirred at the same temperature for 30 minutes.

Diisopropyl ether was added to the stirring mixture to give a precipitate.

The precipitate (130 mg) collected by filtration was dissolved in 1.3 ml of water with sodium bicarbonate and purified by column chromatography on Diaion HP-20 (methanol-water=1:1) to give 70 mg of (6R,7R)-7-((Z)-2-(2-aminothiazol-4-yl)-2-methoxyiminoacetamide)-3-(1-carboxymethylpyridinium-4-ylthiomethyl)-1-oxa-1-dethiaceph-3-em-4-carboxylate.

NMR (D$_2$O) δ (ppm): 3.82 (3H, s), 4.15 (3H, s), 4.37 (2H, s), 4.52 (2H, s), 5.22 (1H, d, J=3.8 Hz), 5.60 (1H, d, J=3.8 Hz), 6.80 (1H, s), 7.98, 8.68 (4H, ABq, J=6.3 Hz).

EXAMPLE 11

Preparation of (6R,7R)-7-((Z)-2-(2-Aminothiazol-4-yl)-2-methoxyiminoacetamide)-3-(1-carboxymethylpyridinium-4-ylthiomethyl)-1-oxa-1-dethiaceph-3-em-4-carboxylate Sodium Salt Step (a): Diphenylmethyl (6R,7R)-7-((Z)-2-(2-Tritylaminothiazol-4-yl)-2-(methoxyiminoacetamide)-3-(1-diphenylmethoxycarbonylmethylpyridinium-4-ylthiomethyl)-1-oxa-1-dethiaceph-3-em-4-carboxylate Iodide 1-Diphenylmethoxycarbonylethyl-4-thiopyridone (30 mg, 0.09 mmol) and NaI (30 mg, 0.2 mmol) were added to a solution of diphenylmethyl (6R,7R)-7-((Z)-2-(2-tritylaminothiazol-4-yl)-2-methoxyiminoacetamide)-3-chloromethyl-1-oxa-1-dethiaceph-3-em-4-carboxylate (75 mg, 0.088 mmol) prepared in the step (a) of Example 10 in N,N-dimethylformamide, and the mixture was stirred at room temperature for 15 minutes.

The resulting mixture was diluted with 3.8 ml of ethyl acetate, washed with water and 1N hydrochloride acid and water successively, and dried over magnesium sulfate.

Removal of solvents in vacuo gave 90 mg of crude diphenylmethyl (6R,7R)-7-((Z)-2-(2-tritylaminothiazol-4-yl)-2-methoxyiminoacetamide)-3-(1-diphenylmethoxycarbonylmethylpyridinium-4-ylthiomethyl)-1-oxa-1-dethiaceph-3-em-4-carboxylate iodide.

Step (b): (6R,7R)-7-((Z)-2-(2-Aminothiazol-4-yl)-2-methoxyiminoacetamide)-3-(1-carboxymethylpyridinium-4-ylthiomethyl)-1-oxa-1-dethiaceph-3-em-4-carboxylate Sodium Salt Trifluoroacetic acid (1.0 ml) was added to a mixture of the product (90 mg) from the step (a) and anisole (0.27 ml) at 0°–5° C., and the resulting solution was stirred at the same temperature for 40 minutes.

Diisopropyl ether was added to the stirring mixture to give a precipitate.

The precipitate (65 mg) collected by filtration was dissolved in 2.0 ml of water with sodium bicarbonate and purified by column chromatography on Diaion HP-20 (methanol-water=1:4) to give 30 mg of (6R,7R)-7-((Z)-2-(2-aminothiazol-4-yl)-2-methoxyiminoacetamide)-3-(1-carboxymethylpyridinium-4-ylthiomethyl)-1-oxa-1 -dethiaceph-3-em-4-carboxylate sodium salt.

NMR (D$_2$O) δ (ppm): 3.90 (3H, s), 4.40 (2H, s), 4.58 (2H, s), 5.10 (2H, s), 5.30 (1H, d, J=4 Hz), 5.60 (1H, d, J=4 Hz), 7.10 (1H, s), 7.75, 8.45 (4H, ABq, J=7 Hz).

EXAMPLE 12

Preparation of (6R,7R)-7-((Z)-2-(2-Aminothiazol-4-yl)-2-ethoxyiminoacetamide)-3-(1-carboxymethylpyridinium-4-ylthiomethyl)-1-oxa-1-dethiaceph-3-em-4-carboxylate Sodium Salt Step (a):

Diphenylmethyl (6R,7R)-7-((Z)-2-(2-Tritylaminothiazol-4-yl)-2-ethoxyiminoacetamide)-3-(1-diphenylmethoxycarbonylmethylpyridinium-4-ylthiomethyl)-1-oxa-1-dethiaceph-3-em-4-carboxylate Iodide 1-Diphenylmethoxycarbonylethyl-4-thiopyridone (37 mg, 0.11 mmol) and NaI (30 mg, 0.2 mmol) were added to a solution of diphenyl methyl (6R,7R)-7-((Z)-2-(2-tritylaminothiazol-4-yl)-2-ethoxyiminoacetamide)-3-chloromethyl-1-oxa-1-dethiaceph-3-em-4-carboxylate (84 mg, 0.1 mmol), which was prepared in the similar manner as in the step (a) of Example 10 using (Z)-2-(2-tritylaminothiazol-4-yl)-2-ethoxyiminoacetic acid instead of (Z)-2-(2-tritylaminothiazol-4-yl)-2-ethoxyiminoacetic acid, in 0.84 ml of N,N-dimethylformamide, and the mixture was stirred at room temperature for 15 minutes. The resulting mixture was diluted with 4.2 ml of ethyl acetate, washed with water and 1N hydrochlorid acid and water successively, and dried over magnesium sulfate.

Removal of solvents in vacuo gave 110 mg of crude diphenylmethyl (6R,7R)-7-((Z)-2-(2-tritylaminothiazol-4-yl)-2-ethoxyiminoacetamide)-3-(1-diphenylmethoxycarbonylmethylpyridinium-4-ylthiomethyl)-1-oxadethiaceph-3-em-4-carboxylate iodide.

Step (b): (6R,7R)-7-((Z)-2-(2-Aminothiazol-4-yl)-2-ethoxyiminoacetamide)-3-(1-carboxymethylpyridinium-4-ylthiomethyl)-1-oxa-1-dethiaceph-3-em-4-carboxylate Sodium Salt Trifluoroacetic acid (1.1 ml) was added to a mixture of the product (110 mg) from the step (a) and anisole (0.33 ml) at 0°–5° C., and the resulting solution was stirred at the same temperature for 40 minutes.

Diisopropyl ether was added to the stirring mixture to give a precipitate.

The precipitate (60 mg) collected by filtration was dissolved in 1.0 ml of water with sodium bicarbonate and purified by column chromatography on Diaion HP-20 (methanol-water=1:4) to give 30 mg of (6R,7R)-7-((Z)-2-(2-aminothiazol-4-yl)-2-ethoxyiminoacetamide)-3-(1-carboxymethylpyridinium-4-ylthiomethyl)-1-oxa-1-dethiaceph-3-em-4-carboxylate sodium salt.

NMR (D$_2$O) δ (ppm): 1.35 (3H, t, J=8 Hz), 4.30 (2H, q, J=8 Hz), 4.40 (2H, s), 4.60 (2H, s), 5.10 (2H, s), 5.23 (1H, d, J=4 Hz), 5.60 (1H, d, J=4 Hz), 7.06 (1H, s), 7.76, 8.45 (4H, ABq, J=9 Hz).

EXAMPLE 13

Preparation of (6R,7R)-7-((Z)-2-(2-Aminothiazol-4-yl)-2-carboxymethoxyiminoacetamide)-3-(1-methylpyridinium-4-ylthiomethyl)-1-oxa-1-dethiaceph-3-em-4-carboxylate Sodium Salt Step (a): Diphenylmethyl (6R,7R)-7-((Z)-2-(2-Tritylaminothiazol-4-yl)-2-diphenylmethoxycarbonylmethoxyiminoacetamide)-3-(1-methylpyridinium-4-ylthiomethyl)-1-oxa-1-dethiaceph-3-em-4-carboxylate Iodide 1-Methyl-4-thiopyridone (25 mg, 0.2 mmol) and NaI (60 mg, 0.4 mmol) were added to a solution of diphenylmethyl (6R,7R)-7-((Z)-2-(2-tritylaminothiazol-4-yl)-2-diphenylmethoxycarbonylmethoxyiminoacetamide)-3-chloromethyl-1-oxa-dethiaceph-3-em-4-carboxylate (206 mg, 0.2 mmol), which was prepared in the similar manner as in the step (a) of Example 10 using (Z)-2-(2-tritylaminothiazol-4-yl)-2-diphenylmethoxycarbonylmethoxyiminoacetic acid instead of (Z)-2-(2-tritylaminothiazol-4-yl)-2-methoxyiminoacetic acid, in 1.67 ml of N,N-dimethylformamide, and the mixture was stirred at room temperature for 15 minutes.

The resulting mixture was diluted with 8.4 ml of ethyl acetate and 8.4 ml of chloroform, washed with water and 1N hydrochloric acid and water successively, and dried over magnesium sulfate. Removal of solvents in vacuo gave 200 mg of crude diphenylmethyl (6R,7R)-7-((Z)-2-(2-tritylaminothiazol-4-yl)-2-diphenylmethoxycarbonylmethoxyiminoacetamide)-3-(1-methylpyridinium-4-ylthiomethyl)-1-oxa-1-dethiaceph-3-em-4-carboxylate iodide.

Step (b): (6R,7R)-7-((Z)-2-(2-Aminothiazol-4-yl)-2-carboxymethoxyiminoacetamide)-3-(1-methylpyridinium-4-ylthiomethyl)-1-oxa-1-dethiaceph-3-em-4-carboxylate Sodium Salt Trifluoroacetic acid (2.0 ml) was added to a mixture of the product (200 mg) from the step (a) and anisole (0.6 ml) at 0°-5° C., and the resulting solution was stirred at the same temperature for 40 minutes.

Diisopropyl ether was added to the stirring mixture to give a precipitate.

The precipitate (130 mg) collected by filtration was dissolved in 1.3 ml of water with sodium bicarbonate and purified by column chromatography on Diaion HP-20 (methanol-water=1:4) to give 60 mg of (6R,7R)-7-((Z)-2-(2-aminothiazol-4-yl)-2-carboxymethoxyiminoacetamide)-3-(1-methylpyridinium-4-ylthiomethyl)-1-oxa-1-dethiaceph-3-em-4-carboxylate sodium salt.

NMR (D$_2$O) δ (ppm): 4.20 (3H, s), 4.35–4.65 (6H), 5.30 (1H, d, J=4 Hz), 5.60 (1H, d, J=4 Hz), 6.95 (1H, s), 7.80, 8.40 (4H, ABq, J=8 Hz).

EXAMPLE 14

Preparation of (6R,7R)-7-((Z)-2-(2-Aminothiazol-4-yl)-2-(2-carboxyprop-2-oxyimino)acetamide-3-(1-methylpyridinium-4-ylthiomethyl)-1-oxa-1-dethiaceph-3-em-4-carboxylate Sodium Salt Step (a): Diphenylmethyl (6R,7R)-7-((Z)-2-(2-Tritylaminothiazol-4-yl)-2-(2-diphenylmethoxycarbonylprop-2-oxyimino)-acetamide)-3-(1-methylpyridinium-4-ylthiomethyl)-1-oxa-1-dethiaceph-3-em-4-carboxylate Iodide 1-Methyl-4-thiopyridone (25 mg, 0.2 mmol) and NaI (60 mg, 0.4 mmol) were added to a solution of diphenylmethyl (6R,7R)-7-((Z)-2-(2-tritylaminothiazol-4-yl)-2-(2-diphenylmethoxycarbonylprop-2-oxyiminoacetamide)-3-chloromethyl-1-oxa-1-dethiaceph-3-em-4-carboxylate (210 mg, 0.2 mmol), which was prepared in the similar manner as in the step (a) of Example 10 using (Z)-2-(2-tritylaminothiazol-4-yl)-2-(2-diphenylmethoxycarbonylprop-2-oxyimino)acetic acid instead of (Z)-2-(2-tritylaminothiazol-4-yl)-2-methoxyiminoacetic acid, in 2.1 ml of N,N-dimethylformamide, and the mixture was stirred at room temperature for 15 minutes.

The resulting mixture was diluted with 8.4 ml of ethyl acetate and 8.4 ml of chloroform, washed with water and 1N hydrochloride acid and water successively, and dried over magnesium sulfate. Removal of solvent in vacuo gave 200 mg of crude diphenylmethyl (6R,7R) -7-((Z)-2-(2-tritylaminothiazol-4-yl)-2-(2-diphenylmethoxycarbonylprop-2-oxyimino)-acetamide)-3-(1-methylpyridinium-4-ylthiomethyl)-1-oxa-1-dethiaceph-3-em-4-carboxylate iodide.

Step (b): (6R,7R)-7-((Z)-2-(2-Aminothiazol-4-yl)-2-(2-carboxyprop-2-oxyimino)acetamide)-3-(1-methylpyridinium-4-ylthiomethyl)-1-oxa-1-dethiaceph-3-em-4-carboxylate Sodium Salt Trifluoroacetic acid (2.0 ml) was added to a mixture of the product (200 mg) from step (a) and anisole (0.6 ml) at 0°-5° C., and the resulting solution was stirred at the same temperature for 40 minutes.

Diisopropyl ether was added to the stirring mixture to give a precipitate.

The precipitate (140 mg) collected by filtration was dissolved in 1.4 ml of water with sodium bicarbonate and purified by column chromatography on Diaion HP-20 (methanol-water=1:4) to give 70 mg of (6R,7R)-7-((Z)-2-(2-aminothiazol-4-yl)-2-(2-carboxyprop-2-oxyimino)acetamide)-3-(1-methylpyridinium-4-ylthiomethyl)-1-oxa-1-dethiaceph-3-em-4-carboxylate sodium salt.

NMR (D$_2$O) δ (ppm): 1.44 (6H, s), 4.19 (3H, s), 4.26, 4.47 (2H, ABq, J=14 Hz), 4.58 (2H, s), 5.24 (1H, d, J=3.5 Hz), 5.57 (1H, d, J=3.5 Hz), 6.95 (1H, s), 7.82, 8.39 (4H, ABq, J=6.4 Hz).

EXAMPLE 15

Preparation of (6R,7R)-7-((Z)-2-(2-Aminothiazol-4-yl)-2-(2-carboxyprop-2-oxyimino)acetamide-3-((2-fluoroethyl)pyridinium-4-ylthiomethyl)-1-oxa-1-dethiaceph-3-em-4-carboxylate Step (a): Diphenylmethyl (6R,7R)-7-((Z)-2-(2--Tritylaminothiazol-4-yl)-2-(2-diphenylmethoxycarbonylprop-2-oxyimino)-acetamide)-3-((2-fluoroethyl)-pyridinium-4-ylthiomethyl)-1-oxa-1-dethiaceph-3-em-4-carboxylate Iodide 1-(2-Fluoroethyl)-4-thiopyridone (13 mg, 0.08 mmol) and NaI (30 mg, 0.2 mmol) were added to a solution of diphenylmethyl (6R,7R)-7-((Z)-2-(2-tritylaminothiazol-4-yl)-2-(2-diphenylmethoxycarbonylprop-2-oxyiminoacetamide)-3-chloromethyl-1-oxa-1-dethiaceph-3-em-4-carboxylate (83 mg, 0.08 mmol) prepared in the step (a) of Example 14 in 0.85 ml of N,N-dimethylformamide, and the mixture was stirred at room temperature for 15 minutes.

The resulting mixture was diluted with 4.3 ml of ethyl acetate, washed with water and 1N hydrochloric acid and water successively, and dried over magnesium sulfate.

Removal of solvents in vacuo gave 85 mg of crude diphenylmethyl (6R,7R)-7-((Z)-2-(2-tritylaminothiazol-4-yl)-2-(2-diphenylmethoxy-carbonylprop-2-oxyimino)acetamide)-3 -(1-(2-fluoro-ethyl)pyridinium-4-ylthiomethyl)-1-oxa-1-dethiaceph-3-em-4-carboxylate iodide.

Step (b): (6R,7R)-7-((Z)-2-(2-Aminothiazol-4-yl)-2-(2-carboxyprop-2-oxyiminoacetamide)-3-(1-(2-fluoroethyl)pyridinium-4-ylthiomethyl)-1-oxa-1-dethiaceph-3-em-4-carboxylate Sodium Salt Trifluoroacetic acid (0.85 ml) was added to a mixture of the product (85 mg) from the step (a) and anisole (0.27 ml) at 0°–5° C., and the resulting solution was stirred at the same temperature for 40 minutes.

Diisopropyl ether was added to the stirring mixture to give a precipitate.

The precipitate (45 mg) collected by filtration was dissolved in 1.0 ml of water with sodium bicarbonate and purified by column chromatography on Diaion HP-20 (methanol-water=1:4) to give 28 mg of (6R,7R)-7-((Z)-2-(2-aminothiazol-4-yl)-2-(2-carboxyprop-2-oxyimino)acetamide)-3-(1 -(2-fluoroethyl)pyridinium-4-ylthiomethyl)-1-oxa-1-dethiaceph-3-em-4-carboxylate sodium salt.

NMR (D$_2$O) δ (ppm): 1.57 (6H, s), 4.15–4.65 (4H), 5.15–5.35 (2H), 5.38 (1H, d, J=3.6 Hz), 5.70 (1H, d, J=3.6 Hz), 7.06 (1H, s), 8.00, 8.59 (4H, ABq, J=7.2 Hz).

EXAMPLE 16

Preparation of
(6R,7R)-7-((Z)-2-(s-Aminothiazol-4-yl)-2-(2-carboxyprop-2-oxyimino)acetamide-3-((2,2,2-trifluoroethyl)-pyridinium-4-ylthiomethyl)-1-oxa-1-dethiaceph-3-em-4-carboxylate Sodium Salt Step (a): Diphenylmethyl (6R,7R)-7-((Z)-2-(2-Tritylaminothiazol-4-yl)-2-(2-diphenylmethoxycarbonylprop-2-oxyimino)acetamide)-3-((2,2,2-trifluoroethyl)-pyridinium-4-ylthiomethyl)-1-oxa-1-dethiaceph-3-em-4-carboxylate Iodide 1-(2,2,2-Trifluoroethyl)-4-thiopyridone (44 mg, 0.25 mmol) and NaI (60 mg, 0.4 mmol) were added to a solution of diphenylmethyl (6R,7R)-7-((Z)-2-(2-tritylaminothiazol-4-yl)-2-(2-diphenylmethoxycarbonylprop-2-oxyiminoacetamide)-3-chloromethyl-1-oxa-1-dethiaceph-3-em-4-carboxylate (245 mg, 0.22 mmol) prepared in the step (a) of Example 14 in 2.5 ml of N,N-dimethylformamide, and the mixture was stirred at room temperature for 15 minutes.

The resulting mixture was diluted with 12.5 ml of ethyl acetate, washed with water and 1N hydrochloric acid and water successively, and dried over magnesium sulfate.

Removal of solvents in vacuo gave 300 mg of crude diphenylmethy (6R,7R)-7-((Z)-2-(2-tritylaminothiazol-4-yl)-2-(2-diphenylmethoxycarbonylprop-2-oxyimino)acetamide)-3-(1-(2,2,2-trifluoroethyl)-pyridinium-4-ylthiomethyl)-1-oxa-1-dethiaceph-3-em-4-carboxylate iodide.

Step (b): (6R,7R)-7-((Z)-2-(2-Aminothiazol-4-yl)-2-(2-carboxyprop-2-oxyimino)acetamide)-3-(1-(2,2,2,-trifluoroethyl)pyridinium-4-ylthiomethyl)-1-oxa-1-dethiaceph-3-em-4-carboxylate Sodium Salt Trifluoroacetic acid (3.0 ml) was added to a mixture of the product (300 mg) from the step (a) and anisole (0.9 ml) at 0°–5° C., and the resulting solution was stirred at the same temperature for 40 minutes.

Diisopropyl ether was added to the stirring mixture to give a precipitate.

The precipitate (170 mg) collected by filtration was dissolved in 1.7 ml of water with sodium bicarbonate and purified by column chromatography on Diaion HP-20 (methanol-water=1:4) to give 100 mg of (6R,7R)-7-((Z)-2-(2-aminothiazol-4-yl)-2-(2-carboxyprop-2-oxyimino)acetamide)-3-(1-(2,2,2-trifluoroethyl)-pyridinium-4-ylthiomethyl)-1-oxa-1-dethiaceph-3-em-4-carboxylate sodium salt.

NMR (D$_2$O) δ (ppm): 1.44 (6H, s), 4.35, 4.48 (2H, ABq, J=14 Hz), 4.58 (2H, s), 5.27 (1H, d, J=3.8 Hz), 5.30, 5.32 (2H, ABq, J=3.8 Hz), 6.95 (1H, s), 7.96, 8.57 (4H, d, J=6.8 Hz).

EXAMPLE 17

Preparation of
(6R,7R)-7-[(Z)-2-(2-Aminothiazol-4-yl)-2-(2-carboxyprop-2-oxyimino)acetamide]-(2S)-2-methyl-3-[1-3-(1,3-difluoroprop-2-yl)pyridinium-4-ylthiomethyl]-1-oxade thiaceph-3-em-4-carboxylate Sodium Salt Step (a): Diphenylmethyl (6R,7R)-7-[(Z)-2-(2-Tr itylaminothiazol-4-yl)-2-(2-diphenylmethoxycarbonylprop-2-oxyimino)-acetamide]-(2S)-2-methyl-3-[1-(1,3-difluoroprop-2-yl)pyridinium-4-ylthiomethyl[-1-oxa-1-dethiaceph-3-em-4-carboxylate Iodide 1-(1,3-Difluoroprop-2-yl)-4-thiopyridone (13 mg, 0.97 mmol) and NaI (18 mg, 0.12 mmol) were added to a solution of diphenylmethyl (6R,7R)-7-[(Z)-2-(2-tritylaminothiazol-4-yl)-2-(2-diphenylmethoxycarbonylprop-2-oxyimino)acetamide]-(2S)-2-methyl-3-chloromethyl-1-oxa-1-dethiaceph-3-em-4-carboxylate (65 mg, 0.06 mmol) prepared in the step (a) of Example 1 in 0.65 ml of N,N-dimethylformamide, and the mixture was stirred at room temperature for 15 minutes. The resulting mixture was diluted with 6.5 ml of ethyl acetate, washed with water and 1N hydrochloric acid and water successively, and dried over magnesium sulfate.

Removal of solvents in vacuo gave 80 mg of crude diphenylmethyl (6R,7R)-7-[(Z)-2-(2-tritylaminoth iazol-4-yl)-2-(2-diphenylmethoxy-carbonylprop-2-oxyimino)acetamide]-(2S)-2-methyl-3-[1-(1,3-difluoroprop-2-yl)pyridinium-4-ylthio-methyl]-1-oxa-1-dethiaceph-3-em-4-carboxylate iodide which was used to the next step without further purification.

Step (b): (6R,7R)-7-[(Z)-2-(2-Aminothiazol-4-yl)-2-(2-carboxyprop-2-oxyimino)acetamide]-(2S)-2-methyl-3-[1-(1,3-difluoroprop-2-yl)pyridinium-4-ylthiomethyl]-1-oxa-1-dethiaceph-3-em-4-carboxylate Sodium Salt Trifluoroacetic acid (0.8 ml) was added to a mixture of the product (95 mg) from the step (a) and anisole (0.24 ml) at 0°–5° C., and the resulting solution was stirred at the same temperature for 40 minutes.

Diisopropyl ether was added to the stirring mixture to give a precipitate.

The precipitate (50 mg) collected by filtration was dissolved in 0.5 ml of water with sodium bicarbonate and purified by column chromatography on Diaion HP-20 (methanol-water=4:1) to give 35 mg of (6R,7R)-7-[(Z)-2-(2-aminothiazol-4-yl)-2-(2-carboxyprop-2-oxyimino)acetamide]-(2S)-2-methyl-3-[1-(1,3-difluoroprop-2-yl)-pyridinium-4-ylthiomethyl]-1-oxa-1-dethiaceph-3-em-4-carboxylate sodium salt.

NMR (D$_2$O) δ (ppm): 1.53 (9H), 3.90–5.00 (6H), 5.26 (1H, d, J=4 Hz), 5.30–5.45 (2H, m), 5.63 (1H, d, J=4 Hz), 7.03 (1H, s), 7.85, 8.65 (4H, ABq, J=8 Hz).

EXAMPLE 18

Preparation of
(6R,7R)-7-[(Z)-2-(2-Aminothiazol-4-yl)-2-carboxymethoxyiminoacetamide]-(2S)-2-methyl-3-(1-methylpyridinium-4-ylthiomethyl)-1-oxadethiaceph-3-em-4-carboxylate Sodium Salt Step (a): Diphenylmethyl (6R,7R)-7-[(Z)-2-(2-Tritylaminothiazol-4-yl)-2-(diphenylmethoxycarbonylme thoxyimino)acetamide]-(2S)-2-methyl-3-(1-methyl-pyridinium-4-ylthiomethyl)-1-oxa-1-dethiaceph-3-em-4-carboxylate Iodide 1-Methyl-4-thiopyridone (9 mg, 0.07 mmol) and NaI (23 mg, 0.15 mmol) were added to a solution of diphenylmethyl (6R,7R)-7-[(Z)-2-tritylaminothiazol-4-yl)-2-(diphenylmethoxycarbonylmethoxyimino)acetamide]-(2S)-2-methyl-3-chloromethyl-1-oxa-1-dethiaceph-3-em-4-carboxylate (75 mg, 0.07 mmol), which was prepared in the similar manner as in the step (a) of Example 1 using (Z)-2-(2-tritylaminothiazol-4-yl)-2-(diphenylmethoxycarbonylmethyloxyimino)acetic acid instead of (Z)-2-(2-tritylaminothiazol-4-yl)-2-(2-diphenylmethoxycarbonylprop-2-oxyimino)acetic acid, in 0.75 ml of N,N-dimethylformamide.

The mixture was stirred at room temperature for 15 minutes, then diluted with 3.7 ml of ethyl acetate and 3.7 ml of chloroform, washed with water and 1N hydrochloric acid and water successively, and dried over magnesium sulfate.

Removal of solvents in vacuo gave 83 mg of crude diphenylmethyl (6R,7R-7)-[(Z)-2-(2-tritylaminothiazol-4-yl)-2-(diphenylmethoxycarbonylmethoxyimino)acetamide]-(2S)-2-methyl-3-(1-methylpyridinium-4-ylthiomethyl)-1-oxa-1-dethiaceph-3-em-4-carboxylate iodide, which was used to the next step without further purification.

Step (b): Preparation of (6R,7R)-7-[(Z)-2-(2-Aminothiazol-4-yl)-2-carboxymethoxyiminoacetamide]-(2S)-2-methyl-3-(1-methylpyridinium-4-ylthiomethyl)-1-oxadethiaceph-3-em-4-carboxylate Sodium Salt Trifluoracetic acid (0.83 ml) was added to a mixture of the product (83 mg) from the step (a) and anisole (0.25 ml) at 0°-5° C., and the mixture was stirred at the same temperature for 40 minutes.

Diisopropyl ether was added to the stirring mixture to give a precipitate.

The precipitate (43 mg) collected by filtration was dissolved in 0.5 ml of water with sodium bicarbonate and purified by column chromatography on Diaion HP-20 (methanol-water = 1:4) to give 30 mg of (6R,7R)-7-[(Z)-2-(2-aminothiazol-4-yl)-2-carboxymethoxyiminoacetamide]-(2S)-2-methyl-3-(1-methylpyridinium-4-ylthiomethyl)-1-oxa-1-dethiaceph-3-em-4-carboxylate sodium salt.

NMR (D$_2$O) δ (ppm): 1.50 (3H, d, J=8 Hz), 3.90 (1H, d, J=14 Hz), 4.20 (3H, s), 4.56 (2H, s), 4.60–5.00 (3H), 5.18 (1H, d, J=4 Hz), 5.55 (1H, d, J=4 Hz), 7.03 (1H, s), 7.66, 8.36 (4H, ABq, J=8 Hz).

EXAMPLE 19

Preparation of (6R,7R)-7-[(Z)-2-(2-Aminothiazol-4-yl)-2-carboxymethoxyiminoacetamide]-(2S)-2-methyl-3-[1-(2-fluoroethyl)pyridinium-4-ylthiomethyl]-1-oxa-1-dethiaceph-3-em-4-carboxylate Sodium Salt Step (a): Diphenylmethyl (6R,7R)-7-[(Z)-2-(2-Tritylaminothiazol4-yl)-2-diphenylmethoxycarbonylemethoxyimino)acetamide]-(2S)-2-methyl-3-[1-(2-fluoroethyl)pyridinium-4-ylthiomethyl]-1-oxa-1-dethiaceph-3-em-4-carboxylate Iodide 1-(2-Fluoroethyl)-4-thiopyridin (11 mg, 0.07 mmol) and NaI (23 mg, 0.15 mmol) were added to a solution of diphenylmethyl (6R,7R)-7-[(Z)-2-tritylaminothiazol-4-yl)-2-(diphenylmethoxycarbonylmethoxyimino)acetamide]-(2S)-2-methyl-3-chloromethyl-1-oxa-1-dethiaceph-3-em-4-carboxylate (75 mg, 0.07 mmol) prepared in the step (a) of Example 18 in 0.75 ml N,N-Dimethylformamide, and the mixture was stirred at room temperature for 15 minutes.

The resulting mixture was diluted with 7.5 ml of ethyl acetate, washed with water and 1N hydrochloric acid and water successively, and dried over magnesium sulfate.

Removal of solvents in vacuo gave 80 mg of crude diphenylmethyl (6R,7R)-7-[(Z)-2-(2-tritylaminothiazol-4-yl)-2-(diphenylmethoxycarbonylmethoxyimino)acetamide]-(2S)-2-methyl-3-[1-(2-fluoroethyl)-pyridinium-4-ylthiomethyl]-1-oxa-1-dethiaceph-3-em-4-carboxylate iodide, which was used to the next step without further purification.

Step (b): Preparation of (6R,7R)-7-[(Z)-2-(2-Aminothiazol-4-yl)-2-carboxymethoxyiminoacetamide]-(2S)-2-methyl-3-[1-(2-fluoroethyl)pyridinium-4-ylthiomethyl]-1-oxa-1-dethiaceph-3-em-4-carboxylate Sodium Salt Trifluoroacetic acid (0.8 ml) was added to a mixture of the product (80 mg) from the step (a) and anisole (0.24 ml) at 0°-5° C., and the mixture was stirred at the same temperature for 40 minutes.

Diisopropyl ether was added to the stirring mixture to give a precipitate.

The precipitate (42 mg) collected by filtration was dissolved in 0.5 ml of water with sodium bicarbonate and purified by column chromatography Diaion HP-20 (methanol-water=4:1) to give 42 mg of (6R,7R)-7-[(Z)-2-(2-aminothiazol-4-yl]-2-(carboxymethoxyiminoacetamide-(2S)-2-methyl-3-[1-(2-fluoroethyl)pyridinium-4-yl-thiomethyl]-1-oxa-1-dephiceph-3-em-4-carboxylate sodium salt.

NMR (D$_2$O) δ (ppm:): 1.63 (3H, d, J=8 Hz), 4.06 (1H, d, J=14 Hz), 4.67 (2H, s), 4.70–5.30 (6H), 5.33 (1H, d, J=4 Hz), 5.67 (1H, d, J=4 Hz), 7.16 (1H, s), 7.85, 8.60 (4H, ABq, J=8 Hz).

EXAMPLE 20

Preparation of (6R,7R)-7-[DL-2-(2-Aminothiazol-4-yl)-2-(4-ethyl-2,3-dioxopyperadin-1-ylcarboxamide)acetamide]-3-(1-methyl-pyridinium-4-ylthiomethyl)-1-oxa1-dethiaceph-3-em-4-carboxylate Step (a): Diphenylmethyl (6R,7R)-7-[DL-2-(2-Tritylaminothiazol-4-yl)-2-(4-ethyl-2,3-dioxopyperadin-1-ylcarboxamide)acetamide]-3-(1-methylpyridinium-4-ylthiomethyl)-1-oxa-1-dethiaceph-3-em-4-carboxylate Iodide 1-Methyl-4-thiopyridone (12 mg, 0.1 mmol) and NaI (30 mg, 0.2 mmol) were added to a solution of diphenylmethyl (6R,7R)-7-[DL-2-(2-tritylaminothiazol-4-yl)-2-(4-ethyl-2,3-dioxopyperadin-1-ylcarboxamide)acetamide]-3-chloromethyl-1-oxa-1-dethiaceph-3-em-4-carboxylate, which was prepared in the similar manner as in the step (a) of Example 10 using 2-(2-tritylaminothiazol-4-yl)-2-methoxyiminoacetic acid, in 0.75 ml of N,N-dimethylformamide.

The resulting mixture was stirred at room temperature for 20 minutes, then diluted with 7.5 ml of chloroform, washed with water and 1N hydrochloric acid and water successively, and dried over magnesium sulfate.

Removal of solvents in vacuo gave 80 mg of the crude diphenylmethylpyperadin-1-ylcarboxamide)acetamide]-3-(1-methylpyridinium-4-ylthiomethyl)-1-oxa-1-dethiacept-3-em-4-carboxylate iodide, which was used to the next step without further purification.

Step (b): (6R,7R)-7-[(DL)-2-(2-Aminothiazol-4-yl)-2-(4-ethyl-2,3-dioxopyperadin-1-ylcarboxamide)acetamide]-3-(1-methylpyridinium-4-ylthiomethyl)-1-oxa-1-dethiaceph-3-em-4-carboxylate Trifluoroacetic acid (0.8 ml) was added to a mixture of the product (80 mg) from the step (a) and anisole (0.24 ml) at 0°–5° C., and the mixture was stirred at the same temperature for 40 minutes. Diisopropyl ether was added to the stirring mixture to give a precipitate.

The precipitate (53 mg) collected by filtration was dissolved in 1.0 ml of water with sodium bicarbonate and purified by column chromatography on Diaion HP-20 (methanol-water=1:1) to give 35 mg of sodium (6R,7R)-7-[DL-2-(2-aminothiazol-4-yl)-2-(4-ethyl-2,3-dioxopyperadin-1-ylcarboxamide)acetamide]-3-(1-methylpyridinium-4-ylthiomethyl)-1-oxa-1-dethiaceph-3-em-4-carboxylate.

NMR (D₂O) δ (ppm:): 1.30 (3H, t, J=7 Hz), 3.20–4.00 (6H), 4.15 (3H, s), 4.20–4.40 (4H), 5.00–5.50 (3H), 6.60 (1H, s), 7.70, 8.30 (4H, ABq, J=7 Hz).

EXAMPLE 21

Preparation of (6R,7R)-7-[(DL)-2-(2-Aminothiazol-4-yl)-2-(4-ethyl-2,3-dioxopyperadin-1-ylcarboxamide)acetamide]-3-(1-carboxymethylpyridinium-4-ylthiomethyl)-1-oxodethiaceph-3-em-4-carboxylate Step (a): Diphenylmethyl (6R,7R)-7-[(DL)-2-Tri tylaminothiazol-4-yl)-2-(4-ethyl-2,3-dioxopyperadin-1-ylcarboxamide)acetamide]-3-(1-tertbutoxycarbonylemethylpyridinium-4-ylthiomethyl)-1-oxa-1-dethiaceph-3-em-4-carboxylate Iodide 1-tert-Butoxycarbonylmethyl-4-thiopyridone (27 mg, 0.12 mmol) and NaI (30 mg, 0.2 mmol) were added a solution of diphenylmethyl(6R,7R)-[DL-2-(2-tritylaminothiazol-4-yl)-2-(4-ethyl-2,3-dioxopyperadine-1-ylcarboxamide)acetamide]-3-chloromethyl-1-oxa-1-dethiaceph-3-em-4-carboxylate prepared in the step (a) of Example 20 in 1.0 ml of N,N-dimethylformamide.

The resulting mixture was stirred at room temperature for 20 minutes, then diluted with 10.0 ml of chloroform, washed with water and 1N hydrochloric acid and water successively, and dried over magnesium sulfate.

Removal of solvents in vacuo gave 140 mg of the crude diphenylmethyl(6R,7R)-7-[DL-2-(2-trityla minothiazol-4-yl)-2-(4-ethyl-2,3-dioxopyperadin-1-ylcarboxamide)acetamide]-3-(1-tert-butoxycarbonyl methylpyrdinium-4-ylthiomethyl)-1-oxa-1-dethiaceph-3-em-4-carboxylate iodide, which was used to the next step without further purification.

Step (b): (6R,7R)-7-[(DL)-2-(2-Aminothiazol-4-yl)-2-(4-ethyl-2,3-dioxopyperadin-1-ylcarboxamide)acetamide]-3-(1-carboxymethylpyridinium-4-ylthiomethyl)-1-oxa-1-dethiaceph-3-em-4-carboxylate Sodium Salt Trifluoroacetic acid (1.4 ml) was added to a mixture of the product (140 mg) from the step (a) and anisole (0.42 ml) at 0°–5° C., and the mixture was stirred at the same temperature for 1 hour. Diisopropyl ether was added to the stirred solution to give a precipitate.

The precipitate (95 mg) collected by filtration was dissolved in 1.0 ml of water with sodium bicarbonate and purified by column chromatography on Diaion HP-20 (methanol-water=1:1) to give 55 mg of sodium (6R,7R)-7-[(Z)-2-(2-aminothiazol-4yl)-2-(4-ethyl-2,3-dioxopyperadin-1-ylcarboxamide)acetamide]-3-(1-carboxymethylpyridinium-4-ylthiomethyl)-1-oxa-1-dethiaceph-3-em-4-carboxylate.

NMR (D₂O)δ (ppm:): 1.20 (3H, t, J=8 Hz), 3.20–4.00 (6H), 4.00–4.50 (4H), 4.90–5.40 (5H), 6.60 (1H, s), 7.65, 8.25 (4H, ABq, J=8 Hz).

What is claimed is:

1. A 1-oxa-1-dethia-cephalosporin compound represented by the general formula (I):

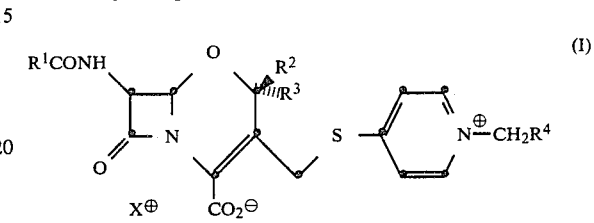

wherein R¹ is a group of the formula:

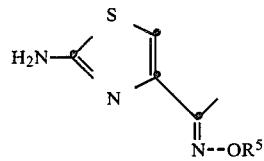

where R⁵ is a carboxymethyl group of a 2-carboxy isopropyl group, either one of R² and R³ is a hydrogen atom and the other a methyl group; R⁴ is a hydrogen atom, a methyl group, a carboxyl group, or a monofluoromethyl group; X⊕ is a cation; and a pharmaceutically acceptable hydrate, salt or ester thereof.

2. A compound of claim 1 having the structure:

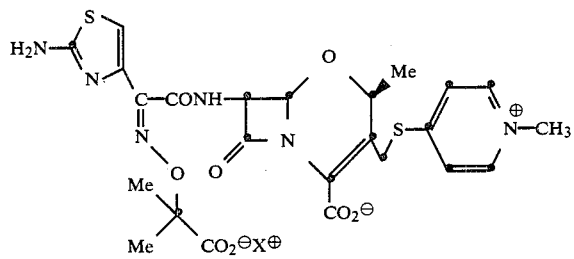

3. A pharmaceutical composition for antibacterial use comprising a therapeutically effective amount of a compound of claim 1 and a pharmaceutically acceptable carrier.

4. A method of treating bacterial infection in a host comprising administering to said host an antibacterially effective amount of a compound of claim 1, either alone or as the active ingredient together with a pharmaceutically acceptable carrier.

* * * * *